(12) United States Patent
Bayer et al.

(10) Patent No.: US 10,105,493 B2
(45) Date of Patent: Oct. 23, 2018

(54) DRIVE MECHANISM FOR A DRUG DELIVERY DEVICE

(71) Applicant: Sanofi, Paris (FR)

(72) Inventors: Stefan Bayer, Würselen (DE); Wolfgang Pelzer, Kreuzau (DE); Björn Wilden, Simmerath (DE); Philipp Zeitz, Aachen (DE)

(73) Assignee: Sanofi, Paris (FR)

( * ) Notice: Subject to any disclaimer, the term of this patent is extended or adjusted under 35 U.S.C. 154(b) by 350 days.

(21) Appl. No.: 14/783,535

(22) PCT Filed: Apr. 8, 2014

(86) PCT No.: PCT/EP2014/057001
§ 371 (c)(1),
(2) Date: Oct. 9, 2015

(87) PCT Pub. No.: WO2014/166919
PCT Pub. Date: Oct. 16, 2014

(65) Prior Publication Data
US 2016/0045669 A1    Feb. 18, 2016

(30) Foreign Application Priority Data

Apr. 10, 2013  (EP) ..................... 13163109

(51) Int. Cl.
*A61M 5/315*  (2006.01)
*A61M 5/20*   (2006.01)
*A61M 5/31*   (2006.01)

(52) U.S. Cl.
CPC .............. *A61M 5/315* (2013.01); *A61M 5/20* (2013.01); *A61M 5/31511* (2013.01);
(Continued)

(58) Field of Classification Search
CPC .............. A61M 5/315; A61M 5/31543; A61M 5/31511; A61M 5/31541; A61M 5/31583;
(Continued)

(56) References Cited

U.S. PATENT DOCUMENTS 8,357,120 B2    1/2013  Moller et al.

FOREIGN PATENT DOCUMENTS

| EP | 2 452 712 | 5/2012 |
| JP | 2012-501705 | 1/2012 |

(Continued)

OTHER PUBLICATIONS

Rote Liste, "50. Hypophysen-, Hypothalamushormone, andere regulatorische Peptide u. ihre Hemmstoffe," Chapter 50, ed. 2008, 20 pages.

(Continued)

*Primary Examiner* — Amber Stiles
(74) *Attorney, Agent, or Firm* — Fish & Richardson P.C.

(57) ABSTRACT

The present invention relates to a drive mechanism for a drug delivery device for dispensing of a dose of a medicament, and to a respective drug delivery device, wherein the drive mechanism comprises: an elongated housing (20) extending in an axial direction (1, 2), a piston rod (160) to operably engage with a piston (14) of a cartridge (12) to displace the piston (14) in axial distal direction (1), a drive wheel (110) axially fixed to the housing (20), engaged with the piston rod (160) and rotatable relative to the housing (20) for driving the piston rod (160) in distal direction (1), a drive sleeve (30) axially displaceable relative to the drive wheel (110) to rotatably engage with the drive wheel (110) in a distal dose dispensing position and to disengage from the drive wheel (110) in a proximal dose setting position, (Continued)

wherein the drive sleeve (30) is rotatably secured to the housing (20) in the proximal dose setting position by means of a ratchet member (32).

17 Claims, 11 Drawing Sheets

(52) U.S. Cl.
CPC .... *A61M 5/31541* (2013.01); *A61M 5/31543* (2013.01); *A61M 5/31553* (2013.01); *A61M 5/31583* (2013.01); *A61M 2005/3126* (2013.01); *A61M 2205/581* (2013.01); *A61M 2205/582* (2013.01)

(58) Field of Classification Search
CPC ................ A61M 5/31553; A61M 5/20; A61M 2205/581; A61M 2205/582; A61M 2005/3126
See application file for complete search history.

(56) References Cited

FOREIGN PATENT DOCUMENTS

| WO | WO 2006/076921 | 7/2006 | |
|----|----------------|--------|---|
| WO | WO 2006/084876 | 8/2006 | |
| WO | WO 2011/67615 | 6/2011 | |
| WO | WO 2011/68531 | 6/2011 | |
| WO | WO 2011154491 A1 * | 12/2011 | ........ A61M 5/31543 |

OTHER PUBLICATIONS

International Preliminary Report on Patentability in International Application No. PCT/EP2014/057001, dated Oct. 13, 2015, 6 pages.

International Search Report and Written Opinion in International Application No. PCT/EP2014/057001, dated May 23, 2014, 8 pages.

* cited by examiner

A-A

B-B

C-C

D-D

E-E

F-F

G-G

H-H

J-J

K-K

DRIVE MECHANISM FOR A DRUG DELIVERY DEVICE

CROSS-REFERENCE TO RELATED APPLICATIONS

This application is a U.S. national stage application under 35 USC § 371 of International Application No. PCT/EP2014/057001, filed on Apr. 8, 2014, which claims priority to European Patent Application No. 13163109.5, filed on Apr. 10, 2013, the entire contents of which are incorporated herein by reference.

The present invention relates to a drive mechanism for a drug delivery device and to a respective drug delivery device. In particular, the invention relates to an injection device such like a pen-type injector inter alia comprising a single and/or a last-dose limiting mechanism.

BACKGROUND AND PRIOR ART

Drug delivery devices for setting and dispensing a single or multiple doses of a liquid medicament are as such well-known in the art. Generally, such devices have substantially a similar purpose as that of an ordinary syringe.

Drug delivery devices, in particular pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing or a particular cartridge holder, adapted to receive a cartridge at least partially filled with the medicament to be dispensed. The device further comprises a drive mechanism, usually having a displaceable piston rod which is adapted to operably engage with a piston of the cartridge. By means of the drive mechanism and its piston rod, the piston of the cartridge is displaceable in a distal or dispensing direction and may therefore expel a predefined amount of the medicament via a piercing assembly, which is to be releasably coupled with a distal end section of the housing of the drug delivery device.

The medicament to be dispensed by the drug delivery device is provided and contained in a multi-dose cartridge. Such cartridges typically comprise a vitreous barrel sealed in distal direction by means of a pierceable seal and being further sealed in proximal direction by the piston. With reusable drug delivery devices an empty cartridge is replaceable by a new one. In contrast to that, drug delivery devices of disposable type are to be entirely discarded when the medicament in the cartridge has been completely dispensed or used-up.

Document U.S. Pat. No. 8,357,120 B2 discloses for instance an injection device with a torsion spring and a rotatable display. There, a piston rod has a threaded outer surface that engages and co-operates with a threaded portion of the injection device. The piston rod is driven by a drive member that engages a groove in the piston rod. The axial movement of the piston rod is provided by rotating the piston rod in the threaded portion of the injection device. Furthermore, a locking member is located at a rather distal portion, hence close to a dispensing end of the injection device. It may extend along a cartridge or a cartridge holder comprising the medicament to be dispensed.

With typical drug delivery devices of pen-injector type, patients or users got used to set a dose and to subsequently induce a dose dispensing action by means of a dose setting member and a dose dispensing member, that are both located at a proximal end of the device. Taking the hand-held injection device in a closed hand, an injection procedure may then be simply triggered by depressing a proximally located dose dispensing member in distal direction by making use of a thumb.

It is therefore an object of the present invention to provide an improved drive mechanism of a drug delivery device allowing for a rather easy and intuitive setting and dispensing of a well-defined dose of a medicament. It is a further aim to provide a drive mechanism having a dose setting member and a dose dispensing member that are both located at a proximal end section of the device to improve ease of use of the device.

It is a further object to provide a drug delivery device comprising such a drive mechanism and comprising a cartridge sealed with a piston to become operably engaged with a piston rod of such a drive mechanism.

SUMMARY OF THE INVENTION

In a first aspect a drive mechanism for a drug delivery device is provided for dispensing of a dose of a medicament. The drive mechanism comprises an elongated housing extending in an axial direction. Typically, the housing is of substantially tubular or cylindrical shape that allows and supports gripping and operating of the drive mechanism or of the entire drug delivery device by one hand of a user.

The drive mechanism further comprises a piston rod to operably engage with a piston of a cartridge containing the medicament to be dispensed by the drive mechanism. The cartridge comprises a piston, which, by means of a displacement in axial distal direction, serves to expel an amount of the medicament from the cartridge. Said expelled or dispensed amount correlates to the axial displacement of the piston as determined by the respective axially-directed displacement of the drive mechanism's piston rod.

Typically, the piston seals the cartridge in axial proximal direction. The piston rod of the drive mechanism serves to displace the piston of the cartridge in the axial direction. The piston rod is therefore operable to apply distally-directed thrust or pressure to the piston of the cartridge for displacing the same in distal direction for a predetermined distance that corresponds to the respective amount of the medicament, hence to the dose of the medicament to be dispensed.

Additionally, the drive mechanism comprises a drive wheel which is axially fixed to the housing. The drive wheel is also engaged with the piston rod and it is further rotatable relative to the housing for driving the piston rod in distal direction.

Moreover, the drive mechanism comprises a drive sleeve axially displaceable relative to the drive wheel to rotatably engage with the drive wheel in a distal dose dispensing position and to disengage from the drive wheel in a proximal dose setting position. The drive sleeve is axially displaceable relative to the drive wheel and hence relative to the housing between a distal dose dispensing position and the proximal dose setting position.

When in dose setting position, the drive sleeve is disengaged from the drive wheel and may therefore be rotated for dose setting purpose without any interaction with the drive wheel. In its proximal dose setting position, hence in a dose setting mode of the drive mechanism, the drive sleeve is contactless to the drive wheel. When switching the drive mechanism in dose dispensing mode, e.g. by displacing the drive sleeve in axial distal direction towards the drive wheel for operably engaging, hence for rotatably engaging with the drive wheel, a respective dose dispensing rotation or dose dispensing torque of the drive sleeve transfers to the drive wheel, thereby driving the piston rod in distal direction for expelling a predefined amount of the medicament from the cartridge.

The drive sleeve is rotatably secured to the housing in the proximal dose setting position by means of a ratchet member. By means of the ratchet member, the drive sleeve is rotatable relative to the housing in a discrete and step-wise way. Typically, the drive sleeve is rotatable in a dose incrementing direction against the action of a retaining or retracting force while the ratchet member serves to secure and to fix the drive sleeve in consecutive and discrete steps relative to the housing. The ratchet member serves to compensate the retaining or retracting force so that the drive sleeve can be secured and kept in a well-defined rotational configuration that may correspond with the size of a dose to be dispensed.

Typically, the drive sleeve is rotatably secured to the housing only or exclusively when in dose setting position. When displacing the drive sleeve in distal direction towards or into the distal dose dispensing position, the ratchet member becomes substantially ineffective or is overruled and thereby liberates a rotation of the drive sleeve relative to the housing, which may be induced or triggered by the retaining or retracting force acting on the drive sleeve.

Consequently, when in dose dispensing position, the drive sleeve is free to rotate and is further rotatably engaged or rotatably locked to the drive wheel. A rotation of the drive sleeve therefore transfers to the drive wheel and further to a distally-directed displacement of the piston rod. In this way, the drive sleeve and in particular its axial displacement relative to the housing and relative to the drive wheel provides a clutch mechanism that is operable to selectively induce a driving torque to the drive wheel for displacing the piston rod in distal direction for dose dispensing purpose.

Since the ratchet member is exclusively active when the drive sleeve is in its proximal dose setting position, a dose setting of the drive mechanism can be conducted without any interference or interaction with the drive wheel by rotating the drive sleeve which is then operably disconnected and disengaged from the drive wheel. By simultaneously or consecutively coupling the drive sleeve with the drive wheel in a torque transferring way and by liberating the drive sleeve from the housing due to its distally-directed displacement into the distal dose dispensing position not only a clutch mechanism for switching the drive mechanism between dose setting and dose dispensing mode but also an effective interlocking feature can be provided for the drive mechanism that is effective to impede a rotational displacement of the drive wheel and hence a distally-directed displacement of the piston rod when the drive mechanism is in dose setting mode.

According to a further embodiment, the drive sleeve is rotatable in a dose incrementing direction against the action of a spring element when in proximal dose setting position. Hence, the ratchet member which is active when the drive sleeve is in its proximal dose setting position, at least allows for a dose incrementing rotation of the drive sleeve relative to the housing. The ratchet member particularly serves as a unidirectional interlock to impede a self-actuated rotational displacement of the drive sleeve, which may otherwise occur under the action of the tensioned spring element.

Typically, mutual engagement of the ratchet member and the housing is operable to secure and to fix the drive sleeve in well-defined discrete rotational positions, which typically correspond to standard units of the medicament to be dispensed by the drug delivery device. The step size governed by the mutual engagement of the ratchet member with the housing and/or with the drive sleeve may correlate to e.g. an international unit of insulin IU in case the drug delivery device is designed for insulin injection.

The spring element is typically implemented as a helical spring or torsion spring that may be strained by rotating the drive sleeve relative to the housing. Once the drive sleeve is rotated relative to the housing in a dose incrementing direction against the action of said spring element and when the drive sleeve is rotatably secured relative to the housing in said rotated configuration by means of the ratchet member, mechanical energy for dispensing of the dose can be stored in the drive mechanism, in particular by the strained spring element.

Upon release, when the drive sleeve is liberated from the housing it may rotate in an opposite, dose decrementing direction under the action of the previously biased spring element. In this way, the spring element serves as mechanical energy storage means, by way of which a semi- or fully automated dose dispensing can be implemented. Typically, the spring element is strained and biased during a dose setting operation, in which the drive sleeve is located in the proximal dose setting position. Displacing the drive sleeve in dose dispensing direction, its ratchet member-governed coupling to the housing is abrogated and the drive sleeve may rotate in the dose decrementing direction under the action of the spring for transferring a respective torque to the drive wheel.

By means of the spring element permanently coupled and engaged with the drive sleeve and by means of the drive sleeve selectively rotatably engageable with the housing, a dispensing procedure driven by the spring energy can be conducted. In other words, the driving force to be transferred to the piston rod for driving the same in distal direction during a dose dispensing procedure can be completely provided by the spring element previously biased or tensioned during a preceding dose setting procedure.

According to another embodiment, the drive sleeve is rotatable in a dose decrementing direction against the action of the ratchet member when in proximal dose setting position. Hence, mutual engagement of the drive sleeve and the housing by way of the ratchet member is designed such, that the ratchet member effectively impedes a self-activated rotational displacement of the drive sleeve relative to the housing under the effect of the biased spring element when the drive sleeve is in proximal dose setting position. However, when actively applying a force to the drive sleeve in dose decrementing direction, the securing effect of the ratchet member may be overruled. The ratchet member therefore serves to provide a torque or force dependent rotational interlock for the drive wheel relative to the housing.

Applying of a force or torque in dose decrementing direction above a predefined threshold may overrule the effect and action of the ratchet member. In this way, not only a dose incrementing but also a dose decrementing manipulation of the drive sleeve is enabled when the drive mechanism is in dose setting mode. In the event, that a selected dose is too high, a dose correcting, hence a dose incrementing rotation of the drive sleeve is possible and enabled by the ratchet member.

According to another embodiment, the drive sleeve comprises the ratchet member meshing with a first toothed profile of the housing when in proximal dose setting position. The toothed profile of the housing is typically of annular shape and extends on a radially inwardly facing sidewall portion of the housing. Accordingly, the ratchet member of the drive sleeve is radially resiliently deformable to mesh with the housing's first toothed profile.

The ratchet member typically comprises an arc-shaped latch element featuring a radially outwardly extending protrusion with a geometrical shape that corresponds with the first toothed profile's teeth. Typically, the teeth and/or the radially outwardly extending protrusion of the ratchet member are somehow asymmetric in order to provide different mechanical resistance when rotating the drive sleeve in dose incrementing and dose decrementing direction, respectively.

Typically, the shape of the first toothed profile and/or the shape of the ratchet member's protrusion is designed such, that a torque for rotating the drive sleeve in dose decrementing direction must be larger than a torque for rotating the drive sleeve in dose incrementing direction. In this way, a rather smooth and easy dose setting or dose incrementing is provided while dose decrementing or dose correction requires application of a substantive torque above a predefined threshold.

According to another embodiment, the drive sleeve is displaceable in distal direction against the action of a retention spring element axially supported by the housing. By means of the retention spring element, the drive sleeve is kept per default in its proximal dose setting position. For dispensing of a dose, the drive sleeve must be actively displaced in distal direction against the action of said retention spring element.

Typically and for dose dispensing, the drive sleeve has to be actively kept in distal dose dispensing position during the entire dose dispensing process. This may for instance require, that the user of the drug delivery device constantly depresses a respective dose dispensing member during the duration of the dose dispensing process. A premature or early release of e.g. a dose dispensing member may immediately lead to a proximally-directed displacement of the drive sleeve under the action of the retention spring element. Then, the drive sleeve will be immediately decoupled or disengaged from the drive wheel. Consequently, a distally-directed displacement of the piston rod will immediately stop and the drive wheel may repeatedly rotatably engage with the housing by means of the ratchet member. In this way, mechanical energy previously stored in the spring element during a dose setting procedure does not get lost.

Moreover, since keeping of the drive sleeve in the distal dose dispensing position requires a constant application of at least depressing of a dose dispensing member, the user may abrogate or interrupt a dispensing procedure in a very intuitive and easy way, simply by releasing the respective dose dispensing member.

The retention spring element may be axially displaced between the drive sleeve and a respective support of the housing. Moreover, the retention spring element may be integrally formed with the drive sleeve or with the housing. Typically, the retention spring element is of helical shape and may be compressed in axial direction during a dose dispensing procedure. The retention spring element may be located at a distal end of the drive sleeve and may axially abut with a proximal face of a radially inwardly extending flange or rim of the housing. Alternatively, the retention spring element is integrally formed with the housing and axially abuts with a distal abutment face of the drive sleeve, which does not necessarily have to be located at the drive sleeve's distal end but may be located elsewhere, e.g. also in a middle section or at a proximal end of the drive sleeve.

According to another embodiment, the drive mechanism further comprises a dose dispensing member located at a proximal end of the housing. The dose dispensing member is operably engaged with the drive sleeve and it is distally depressible relative to the housing to displace the drive sleeve into the distal dose dispensing position. Here, the dose dispensing member serves as an actuation means to trigger a dose dispensing process. It is in particular the distally depressible dose dispensing member by way of which the drive sleeve is displaceable in distal direction and into the distal dose dispensing direction, typically against the action of the retention spring element. The dose dispensing member, the drive sleeve, the ratchet member and the housing therefore provide an interlock- and release mechanism, by way of which a user may trigger and control a dose dispensing procedure.

Since the dose dispensing member operably engaged with the drive sleeve is located at a proximal end of the housing, distally-directed depression of the dose dispensing member may be governed and induced by a user's thumb.

According to another embodiment, the drive sleeve comprises a crown wheel at its distal end to engage with a corresponding crown wheel of the drive wheel. Respective crown wheels of drive sleeve and drive wheel allow and support an axial displacement of the drive sleeve relative to the drive wheel. The axial extension of the teeth of the drive sleeve's and/or drive wheel's crown wheel is selected such, that during a distally-directed displacement of the drive wheel from its proximal dose setting position into its distal dose dispensing position, the drive sleeve is rotatably coupled and engaged with the drive wheel by means of the corresponding crown wheels before the ratchet member liberates or releases a rotation of the drive wheel relative to the housing. In this way, a rather slip-free clutch mechanism can be provided which effectively prevents dissipation of mechanical energy stored by the helical- or torsion spring element.

According to another embodiment the drive wheel is rotatably locked to the housing with regard to the dose incrementing direction by means of an interlocking member. The interlocking member is engaged with a second toothed profile of the housing. Typically, first and second toothed profiles of the housing are axially separated or axily ofset. Since the drive sleeve is engageable with the drive wheel by its distal end, the second toothed profile cooperating and meshing with the drive wheel's interlocking member is axially separated from the first toothed profile in distal direction.

The interlocking member typically comprises a radially resiliently deformable ratchet or ratchet member featuring a radially outwardly extending protrusion at its free end. When rotating in dose decrementing direction, e.g. during a dose dispensing procedure, the interlocking member meshes with the second toothed profile in a stepwise and discrete way. In particular, the radially outwardly extending protrusion of the interlocking member consecutively engages and meshes with the teeth of the second toothed profile that are adjacently arranged in circumferential direction, in particular at an inside-facing sidewall portion of the housing.

In contrast to the mutual engagement of the drive sleeve's ratchet member with the first toothed profile, the drive wheel's interlocking member is adapted to strictly inhibit a rotation of the drive wheel in the dose incrementing direction. In this way, a backward movement, hence, a proximally-directed displacement of the piston rod can be effectively prevented. Additionally, the engagement of the drive wheel's interlocking member with the housing's second toothed profile also provides an audible feedback to the user during a dose dispensing procedure. When the radially outwardly extending protrusion of the resiliently deformable interlocking member repeatedly meshes and engages with consecutive and adjacent teeth of the second toothed profile, a rather regular clicking noise can be generated to audibly indicate to the user, that a dose dispensing procedure is actually in progress. In this way the interlocking member serves as a kind of dispensing clicker.

In effect, the drive wheel and its engagement with the housing provides a one-way clutch for exclusively displacing the piston rod in distal direction during dose dispensing. During dose setting, wherein the drive sleeve is decoupled from the drive wheel, the drive wheel serves to axially fix the piston rod relative to the housing.

According to another embodiment, the drive wheel comprises a threaded orifice, hence, a centrally located through opening which is threadedly engaged with an outer threaded portion of the piston rod. By means of this threaded engagement, a dose decrementing rotation of the drive wheel transfers into a distally-directed displacement of the piston rod given that the piston rod is rotatably secured to the housing. The lead of the threaded engagement of drive wheel and piston rod further determines a transmission ratio.

Typically, the lead of the threaded orifice and the corresponding lead of the threaded portion of the piston rod is of self-locking type. Hence, applying a distally or proximally-directed force to the piston rod does not transfer into a rotation of the drive wheel. Since the drive wheel is axially fixed to the housing, the piston rod, typically comprising a radially widened pressure foot at its distal end remains in axial abutment with the piston of the cartridge after a dose injection procedure has completed or terminated.

Furthermore, due to its arrangement at a distal end of the drive mechanism, the drive wheel provides a rather direct and immediate radial guidance for the piston rod as well as an axial interlock for the piston rod. A negative impact of mechanical play or backlash between piston rod, drive wheel and housing can therefore be reduced to a minimum, thereby increasing dose setting accuracy as well as dose dispensing accuracy.

According to another embodiment, the piston rod comprises an axially extending radial groove engaged with a radial protrusion of a housing's guiding portion. In this way, the piston rod can be rotatably locked to the housing. Since the housing's radial protrusion engages with the axially extending groove or notch of the piston rod, the piston rod is exclusively slidably displaceable in axial direction relative to the housing in a non-rotating way. Due to its threaded engagement with the axially fixed drive wheel, the piston rod experiences a distally-directed displacement relative to the housing as the drive wheel is rotated in dose decrementing direction.

In alternative embodiments it is conceivable, that the piston rod with its outer threaded portion is threadedly engaged with the housing's guiding portion and wherein the piston rod is rotatably engageable with the drive wheel. In both cases, the piston rod comprises a threaded portion intersected by at least one longitudinally or axially extending groove. In the alternative embodiment said groove is engaged with a correspondingly-shaped radially inwardly extending protrusion or pin of the drive wheel.

In this way, a rotation of the drive wheel equally transfers to a rotation of the piston rod. Due to its threaded engagement with the housing's guiding portion, a rotation of the piston rod then immediately leads to a distally-directed displacement thereof relative to the housing. However, with a rotating piston rod, a radially widened pressure foot axially engaging with a proximal end face of the cartridge's piston should be freely rotatably supported on the distal end of the piston rod.

According to another embodiment, the drive sleeve is rotatable in dose decrementing direction under the action of the spring element when in distal dose dispensing position in order to transfer a driving torque to the drive wheel. By displacing the drive sleeve in distal direction, its ratchet member disengages from the first toothed profile of the housing and hence the drive sleeve is liberated to rotate under the action of the helically-shaped torsion spring. The torsion spring is typically arranged around the drive sleeve and extends also in axial direction.

One end of the torsion spring is typically connected with the drive sleeve while an opposite end of the torsion spring is connected to the housing or to a base member fixedly attached to the housing. Since the drive sleeve is disengaged from the housing when reaching its distal dose dispensing position it is free to rotate according to the action of the spring element. Since the drive sleeve is further rotatably coupled or rotatably engaged with the drive wheel the torque and the rotational movement of the drive sleeve can be unalterably transferred to the drive wheel, thereby driving the piston rod in distal direction and urging the piston of the cartridge further into the interior of the cartridge to expel a predefined amount of the medicament therefrom.

Accordingly, the drive sleeve is alternately engageable with the housing or with the drive wheel for either setting or dispensing of a dose. Typically, disengagement of drive sleeve and housing is only provided after engagement of drive sleeve and drive wheel has been established; and vice versa.

In a further embodiment, the drive mechanism also comprises a dose setting member rotatably supported on the housing at least in dose incrementing direction. In this way, the dose setting member is operable to transfer a dose incrementing torque to the drive sleeve when in dose setting position.

Additionally, the dose setting member may also be rotatable in the opposite direction, hence in dose decrementing direction to reduce a dose already set. By providing a rotation of the dose setting member in both, dose incrementing and dose decrementing directions dose setting as well as dose correction can be provided by a single dose setting member in a very intuitive way. Since dose setting and dose correction takes place in the dose setting mode of the drive mechanism neither dose setting nor does correction has an effect on the axial position of the piston rod.

The dose setting member is typically selectively coupled with the drive sleeve only when the drive mechanism is in dose setting mode. Any rotational displacement of the dose setting member may then be transferred into a respective rotation of the drive sleeve. Typically, the mutual engagement between the housing and the drive sleeve's ratchet member is somewhat asymmetric in order to implement dose incrementing and dose decrementing torques of different magnitude. In this way, setting of a dose, i.e. incrementing of a dose may require to apply a driving torque to the dose setting member which is smaller than an oppositely directed driving torque for rotating the drive sleeve and hence the dose setting member in the opposite, hence dose decrementing direction for e.g. correcting of a previously set dose.

According to a further embodiment the dose setting member is rotatably locked to the housing and is rotatably decoupled from the drive sleeve when the drive sleeve is in dose dispensing position. By decoupling dose setting member and drive sleeve during dose dispensing, the drive sleeve may rotate in the dose decrementing direction without any interaction with the dose setting member. Moreover, by rotatably locking the dose setting member to the housing, any manipulation of the dose setting member of either dose incrementing or dose decrementing type is effectively blocked. This is of particular use in order to provide an end of content mechanism which is operable to impede setting of a dose that would exceed an amount of medicament left in the cartridge.

According to another aspect, the invention also relates to a drug delivery device for dispensing of a dose of a medicament. The drug delivery device comprises a drive mechanism as described above and a cartridge at least partially filled with the medicament to be dispensed by the drug delivery. The cartridge is arranged in the housing of the drive mechanism or in a cartridge holder of the drug delivery device which is fixed to the housing either releasably or non-releasably, e.g. in case of a disposable drug delivery device. Consequently, the drug delivery device comprises a cartridge holder to receive and to accommodate a cartridge filled with the medicament.

In the present context, the distal direction points in the direction of the dispensing and of the device, where, preferably a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member is located at the proximal end of the drug delivery device, which is directly operable by a user to be rotated for setting of a dose and which is operable to be depressed in distal direction for dispensing of a dose.

The drive mechanism particularly serves to displace a piston rod in axial direction for the purpose of dispensing of a dose of a medicament. In addition, the drive mechanism typically comprises components which form part of and have a function in at least one of the following mechanisms: a dose setting mechanism, a last dose limiting mechanism and a dose indicating mechanism. As will be apparent from the embodiments described herein various components of e.g. the drive mechanism also belong to at least one of the dose setting mechanism, the last dose limiting mechanism and/or to the dose indicating mechanism; and vice versa. Hence, the invention as described herein equally refers to and defines a drive mechanism, a dose setting mechanism, a last dose limiting mechanism and/or a dose indicating mechanism of a drug delivery device.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39), des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference numerals used in the appended claims are not to be construed as limiting the scope of the invention.

BRIEF DESCRIPTION OF THE DRAWINGS

In the following, a brief description of the drawings is provided, in which.

DETAILED DESCRIPTION

Figure 1:
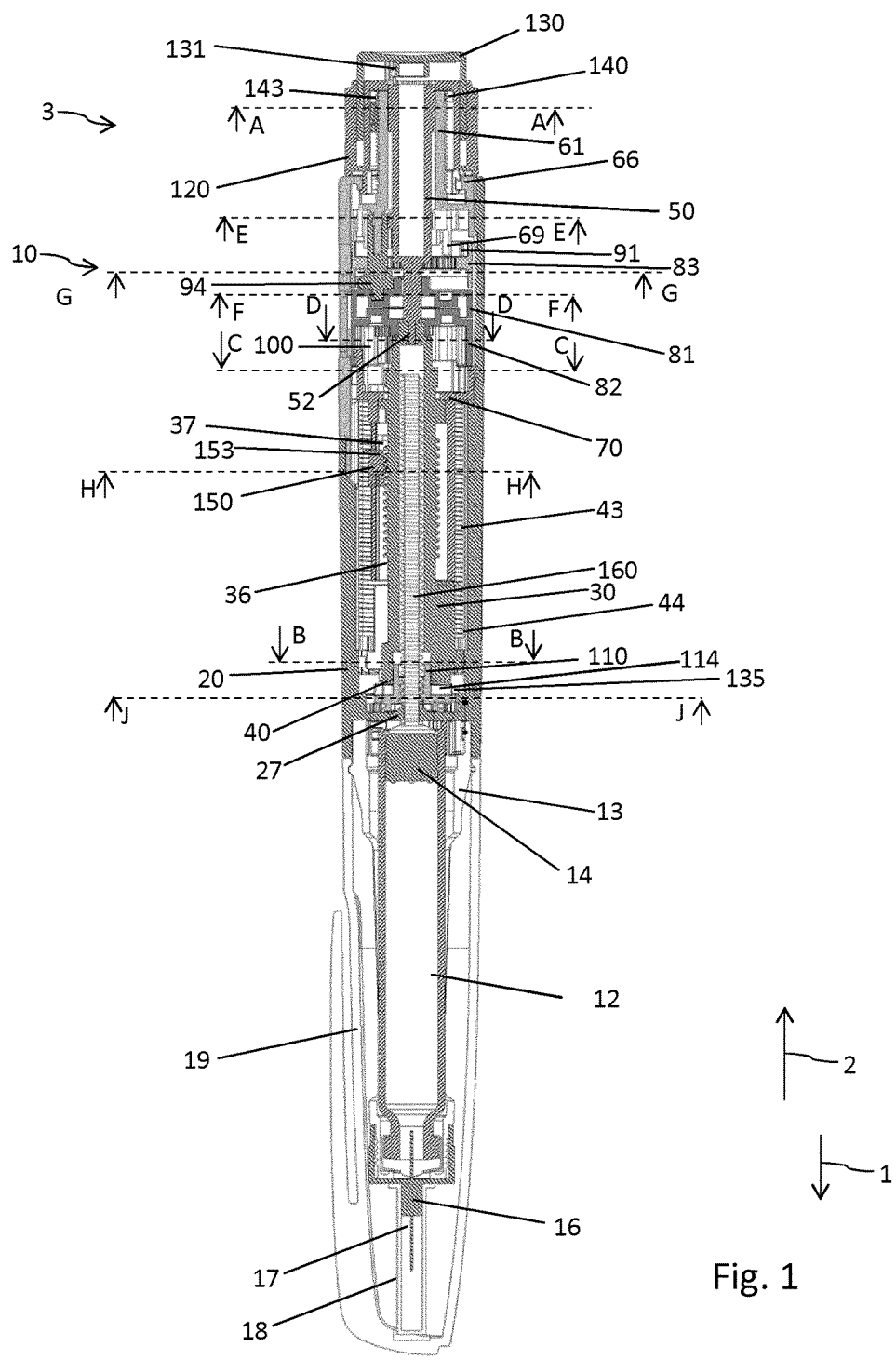
FIG. 1 schematically illustrates the assembled drive mechanism in a pen-type drug delivery device in a longitudinal cut, FIG. 2 perspectively illustrates an exploded view of the complete drug delivery device and its various components.
Figure 2:
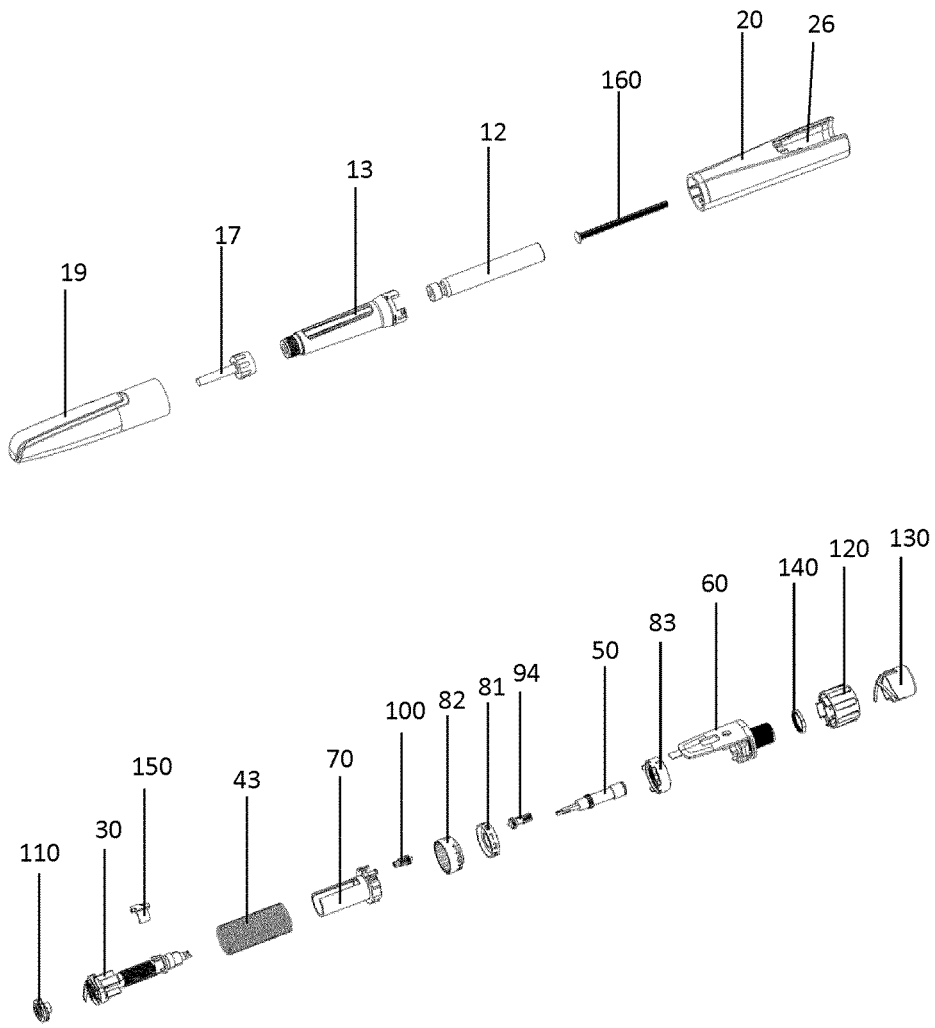

In FIGS. 1 and 2, the complete drug delivery device 10 is illustrated in a longitudinal cross section cut and in an exploded view. The drug delivery device 10 is of pen-injector type and comprises a substantially cylindrical and axially elongated shape. Throughout the Figures the axial distal direction is denoted with reference number 1 and the opposite proximal direction is denoted with reference number 2. The drug delivery device 10 comprises a drive mechanism 3 having comprising a proximal housing 20 or being assembled in a respective body 20 of the drug delivery device 10.

In distal direction the housing 20 is connected with a cartridge holder 13 which is adapted to accommodate and to receive a cartridge 12 containing the medicament to be dispensed by the drug delivery device 10 by way of its drive mechanism 3. The cartridge 12 typically comprises a vitreous barrel of cylindrical or tubular shape and is sealed in distal direction 1 by a pierceable sealing member, such like a septum.

In proximal direction 2, the cartridge 12 is sealed by means of a piston 14 slidably arranged in the barrel of the cartridge 12. The piston 14 typically comprises an elastomeric material, by way of which the proximal end of the cartridge 12 can be effectively sealed in a fluid- and gas-tight manner. The piston 14 of the cartridge 12 is to be operably engaged with a distal end of a piston rod 160 of the drug delivery device's 10 drive mechanism 3. A distally directed displacement of the piston 14 typically induced and governed by the piston rod 160 leads to a respective build up of a fluid pressure inside the cartridge 12. When the distal outlet of the cartridge 12 is connected with e.g. a needle assembly 16 as illustrated in FIG. 1, a predefined amount of the liquid medicament, which equals a previously set dose of the medicament, can be expelled from the cartridge 12 and can be dispensed via an injection needle 17 of the needle assembly 16.

As illustrated in FIG. 1, the needle assembly 16 comprises the double-tipped injection needle 17. The needle assembly 16 is typically removably arranged on a distal end portion of the cartridge holder 13. Here, a distally located socket of the cartridge holder 13 and the needle assembly 16 comprise mutually corresponding threads to screw the needle assembly 16 onto the cartridge holder 13 in a releasable and removable way.

The cartridge holder 13 and hence the cartridge 12 assembled therein is to be protected and covered by a removable protective cap 19. Prior to setting and/or dispensing of a dose, the protective cap 19 as well as an inner needle cap 18 of the needle assembly 16 have to be removed. After dispensing or injecting of the medicament, e.g. into biological tissue, the needle assembly 17 is typically to be disconnected from the cartridge holder 13 and is to be discarded.

The drive mechanism 3 as illustrated in the various FIGS. 3-19 comprises numerous functional and mechanically interengaging components by way of which a dose of variable size can be set and subsequently dispensed. The drive mechanism 3 is of semi-automated type. It comprises a means for storing mechanical energy during a dose setting procedure. Said mechanical energy is then usable for driving the piston rod in distal direction 1 during a dose dispensing procedure. Consequently, it is the device 10 and the drive mechanism 3 that provide mechanical energy and a driving force or driving torque to conduct an injection procedure. Consequently, an injection force does not have to be provided by the user during the dose dispensing process.

Does dispensing requires distally directed advancing of the piston rod 160 relative to the cartridge 12, hence relative to the cartridge holder 13 and relative to the housing 20. The drive mechanism 3 comprises a longitudinally extending hollow shaped drive sleeve 30 that is axially displaceable relative to the housing 20 for switching the drive mechanism 3 between a dose dispensing mode and a dose setting mode. The drive sleeve 30 is rotatably supported on a longitudinal axis 4 that may coincide with the center of the piston rod 160.

Figure 4:
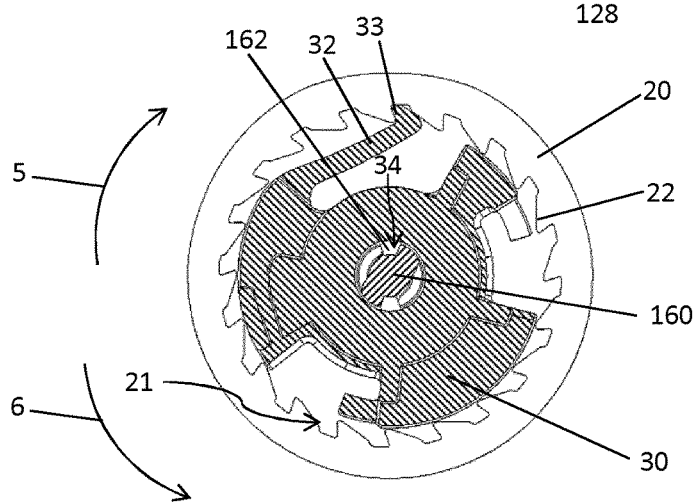
FIG. 4 shows a cross-section along B-D according to FIG. 1.
Figure 6:
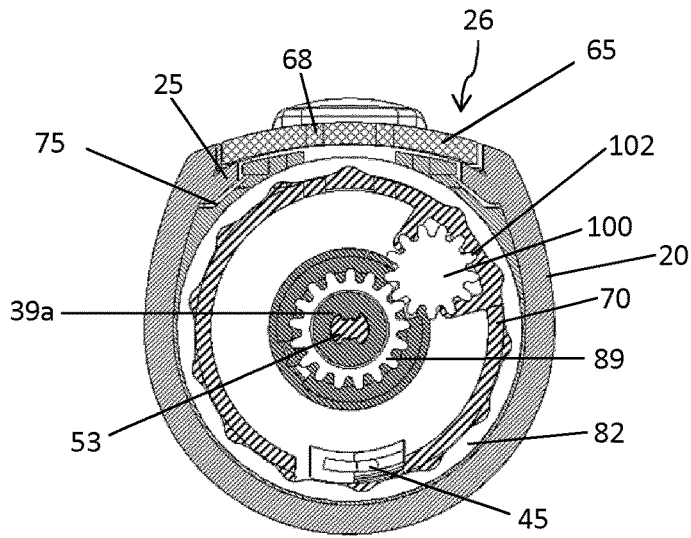
FIG. 6 shows a cross-section through the device along D-D according to FIG. 1.

The drive sleeve 30 is further connected with a spring element 43 featuring a helical shape and acting as a torsion spring. As illustrated in FIGS. 1 and 4, a distal end 44 of the helical spring element 43 is connected with a distal end portion of the drive sleeve 30 while an opposite, proximal end 45 of the helical spring element 43 is connected to a distal base member 70 as illustrated in FIG. 6. The base member 70 is fastened and unmovably fixed to the housing 20. In embodiments without a base member 70 the proximal end 45 of the helical spring element 43 may also be connected to a portion of the housing 20.

As indicated in FIG. 4 the drive sleeve 30 is rotatable in a dose incrementing direction 5 against the action of the helical spring element 43. For setting of a dose, hence for increasing a dose to be set, the drive sleeve 30 rotates in dose incrementing direction 5, thereby straining and biasing the helical spring element 43. In order to store respective mechanical energy in the drive mechanism 3, the drive sleeve 30 is rotatably engaged with the housing 20 by means of a ratchet member 32. The ratchet member 32 comprises an arc-shaped and resiliently deformable circumferentially extending portion featuring a radially outwardly extending catch portion or protrusion 33 that is adapted to engage with a correspondingly shaped first toothed profile 21 located at an inwardly facing sidewall portion of the housing 20.

As shown in FIG. 4, the catch portion or protrusion 33 of the drive sleeve's 30 ratchet member 32 positively engages with consecutive ratchet teeth 22 of the first toothed profile 21. In this way, the drive sleeve 30 can be rotatably secured to the housing 20 at least when located in its proximal dose setting position. The ratchet member 32 is adapted to prevent a self-actuating rotation of the drive sleeve 30 in dose decrementing direction 6 under the effect of the helical spring element 43.

However, the shape of the ratchet member's 32 catch portion 33 and the shape or slope of the various ratchet teeth 22 are designed such that the drive sleeve 30 may also be rotated in a dose decrementing direction 6 if a respective torque above a predefined threshold is applied to the drive sleeve 30. In this way, a dose correction can be conducted even if the drive sleeve 30 is rotatably secured to the housing 20 by means of the ratchet member 32.

Displacement of the drive sleeve 30 in distal direction 1 disengages the ratchet member 32 from the first tooth profile 21. Consequently, when the drive sleeve 30 is in the distal dose dispensing position it is free to rotate in dose decrementing direction 6 under the effect of the helical spring element 43.

As further illustrated in FIG. 4, the piston rod 160 axially extends through a central and longitudinally extending bore 34 of the drive sleeve 30. The drive sleeve 30 may therefore also act as a linear guide for the piston rod 160.

Figure 13:
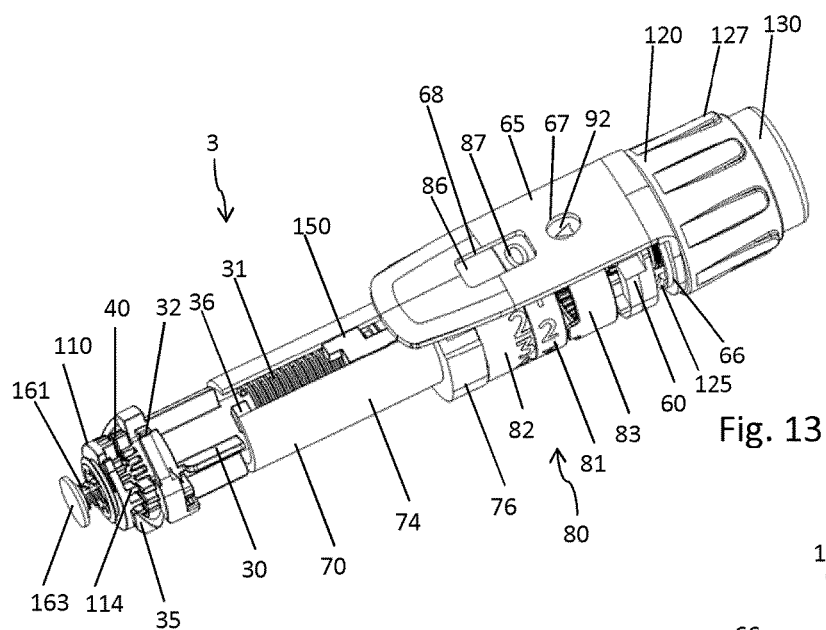
FIG. 13 shows an isolated and perspective illustration of the drive mechanism.
Figures 15, 16:
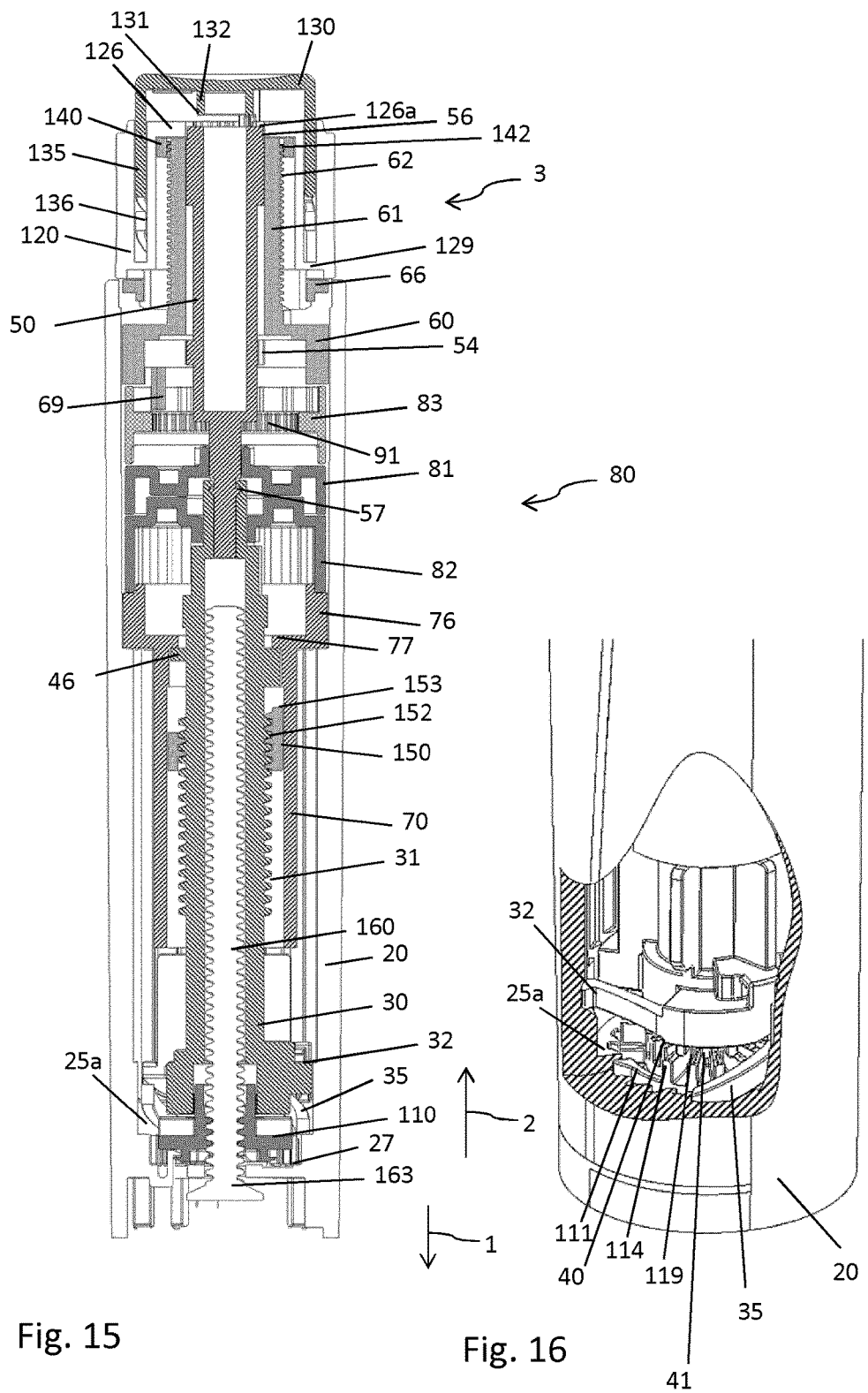
FIG. 16 shows a partially cut view through a distal end of the drive mechanism.

As further illustrated in FIGS. 13 and 16 the drive sleeve 30 comprises at least one retention spring element 35 at its distal end that is operable to axially engage and to axially abut against a radially inwardly extending flange 25a of the housing 20. In this way, the drive sleeve 30 is kept in the proximal dose setting position per default. A distally directed displacement of the drive sleeve 30 may therefore act against said at least one retention spring element 35. Bringing and keeping the drive sleeve 30 into the distal dose dispensing position therefore requires to constantly apply a respective thrust or pressure in distal direction 1 to the drive sleeve 30.

Figure 5:
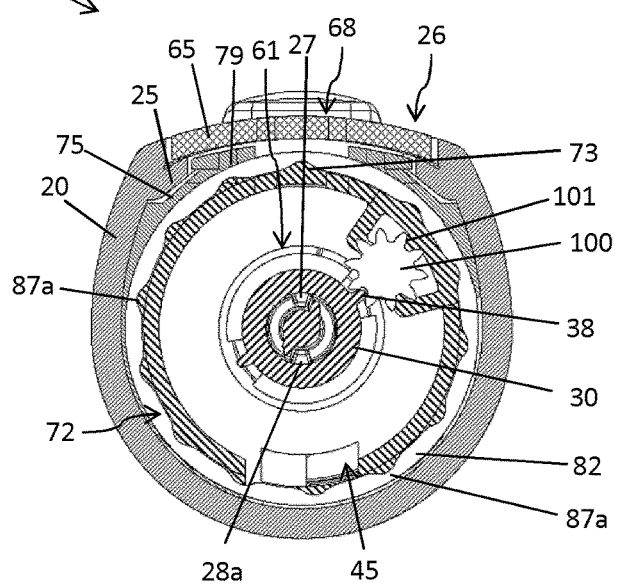
FIG. 5 shows a cross-section through the device along C-C according to FIG. 1.
Figure 12:
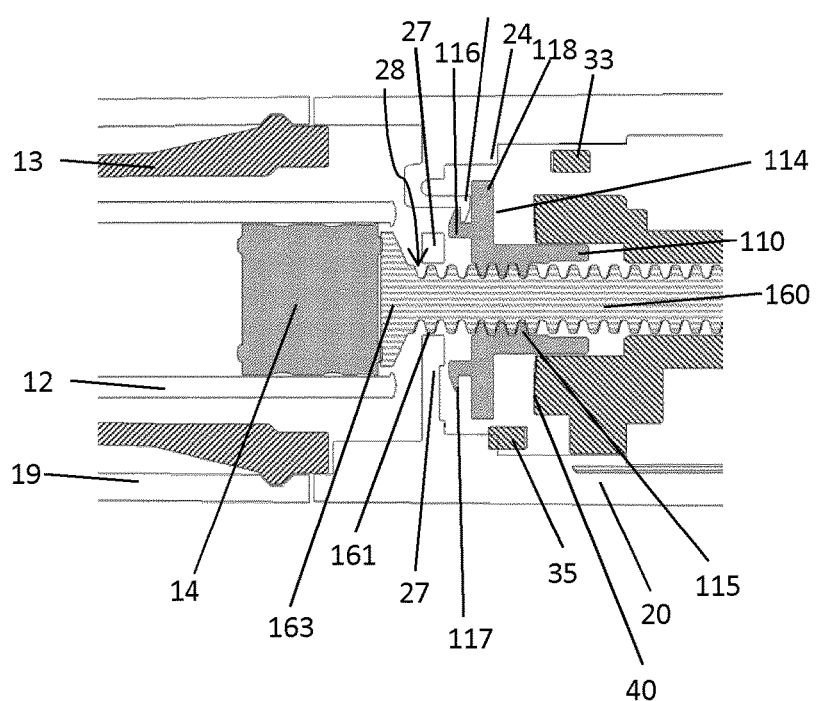
FIG. 12 shows a longitudinal and enlarged cross section of the drive wheel engaging with the piston rod.
Figure 12:

A distally directed displacement of the drive sleeve 30 is limited by an axial abutment with a drive wheel 110 that is axially fixed to the housing 20 as illustrated in the cross-section according to FIG. 12. The drive wheel 110 is rotatably supported relative to the housing 20. In particular, the housing 20 comprises a radially inwardly extending guiding portion 27 featuring a central orifice 28 through which the threaded piston rod 160 extends. The piston rod 160 as further illustrated in FIG. 4 comprises two diametrically oppositely located radially inwardly and axially extending grooves 162 that engage with a correspondingly shaped radially inwardly extending protrusion 28a of the guiding portion 27 as indicated in FIG. 5.

The drive wheel 110 is axially fixed to the housing 20 by means of a positive engagement with a radially inwardly extending fixing member 29 having a radially inwardly extending latch portion to engage with a correspondingly shaped fastening or latch element 116 distally and radially outwardly extending from a distal flange portion 118 of the drive wheel 110. As indicated in FIG. 12, the housing's fixing member 29 is axially constrained between the latch element 116, its radially outwardly extending protrusion 117 and the radially outwardly extending flange portion 118 of the drive wheel 110. In this way, the drive wheel 110 is axially constrained and axially fixed to the housing 20 but may rotate with relative to the housing 20 with the longitudinal or central axis 4 as an axis of rotation.

Figure 11:
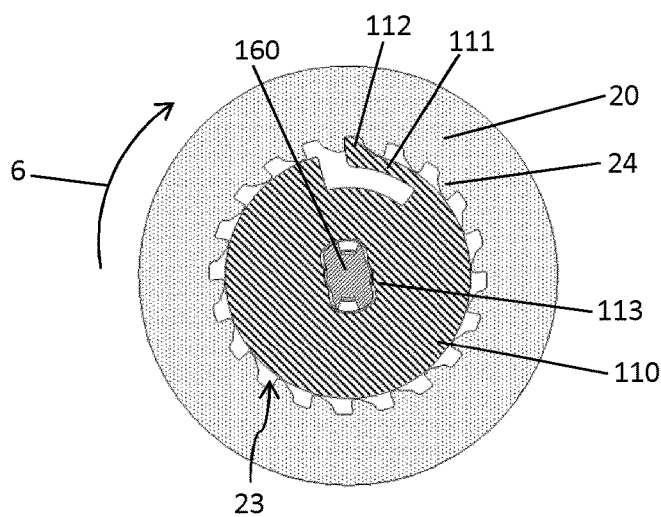
FIG. 11 shows a cross-section along J-J according to FIG. 1.

The mutual engagement of the drive wheel 110 with the fixing member 29 of the housing 20 however allows for a free rotation of the drive wheel 110 at least in a dose decrementing direction 6, as indicated in FIG. 11. As shown there, the drive wheel 110 comprises a circumferentially extending resiliently deformable interlocking member 111 featuring a radially outwardly extending ratchet tooth or protrusion 112 to engage with a second toothed profile 23 of the housing 20. The second toothed profile 23 comprises numerous ratchet teeth 24 radially inwardly protruding from an inward facing sidewall portion of the housing 20. By means of the mutual engagement of the drive wheel's 110 interlocking member 111 with the second toothed profile 23, only a unidirectional rotation of the drive wheel 110, namely in dose decrementing direction 6 is allowed if a respective torque acts on the drive wheel 110.

The ratchet tooth 112 of the interlocking member 111 as well as the shape and design of the various ratchet teeth 24 are designed such, that a dose incrementing rotation of the drive wheel 110 relative to the housing 20 is strictly blocked. In this way, a proximally directed displacement of the piston rod 160 relative to the housing 20 can be effectively prevented.

As it is further indicated in FIG. 12, the piston rod 160 comprises an outer threaded portion 161 threadedly engaged with a correspondingly shaped inner thread 115 of the drive wheel 110. Hence, the drive wheel 110 comprises a central orifice 113 to threadedly engage with the threaded portion 161 of the piston rod. By means of its groove 162 the piston rod 160 is rotatably locked to the housing 20 via the radially inwardly extending protrusions 28a thereof. If the drive wheel 110 rotates in dose decrementing direction 6 the axial fixing of the drive wheel 110 to the housing 20 and its threaded engagement with the piston rod 160 then leads to a distally directed but non-rotative and hence sliding movement of the piston rod 160.

Consequently, the radially widened pressure foot 163 located at a distal end of the piston rod 160 serves to exert distally directed pressure to the piston 14 for driving the same in distal direction 1 relative to the barrel of the cartridge 12. A rotation of the drive wheel 110 therefore directly transfers into a distally directed displacement of the piston rod 160.

Drive sleeve 30 and drive wheel 110 can be selectively coupled and decoupled to transfer angular momentum therebetween. The drive wheel 110 comprises a crown wheel 114 facing in proximal direction to engage with a correspondingly shaped crown wheel 40 of the drive sleeve 30 provided on a distal end of the drive sleeve 30. By means of displacing the drive sleeve 30 in distal direction 1, hence into its distal dose dispensing position, mutually corresponding crown wheels 40, 114 of drive sleeve 30 and drive wheel 110 mutually engage in a torque transferring way. In this way, a dose decrementing rotation 6 of the drive sleeve 30 can be directly transferred into a respective dose decrementing rotation of the drive wheel 110.

The axial dimensions of mutually corresponding teeth 41, 119 of the drive sleeve's 30 crown wheel 40 and the drive wheel's 110 crown wheel 114 is designed such, that respective crown wheels 40, 114 already engage and rotatably lock even before the drive sleeve 30 reaches the distal dose dispensing position. During a distally directed dose dispensing displacement of the drive sleeve 30 the crown wheels 40, 114 mutually engage before the ratchet member 32 of the drive sleeve 30 disengages from the first toothed profile 21 of the housing 20. In this way, a rather slip-free alternative rotational engagement and rotational disengagement of the drive sleeve 30 with the drive wheel 110 and housing 20 can be achieved.

Figure 17:
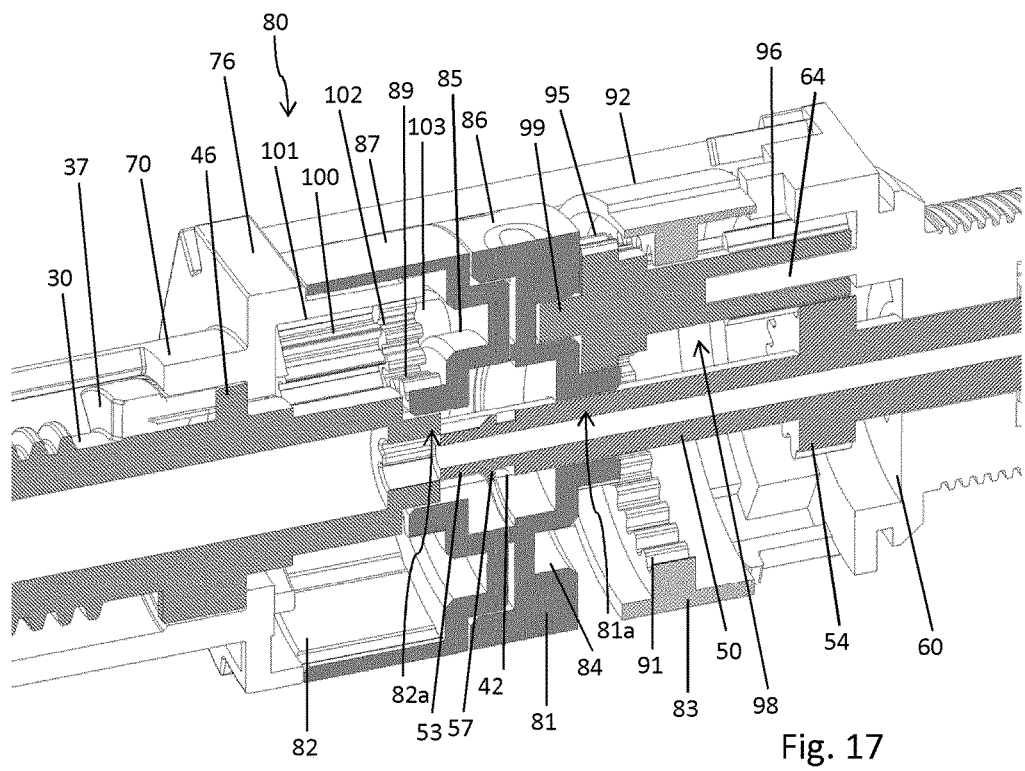
FIG. 17 shows a perspective and longitudinally cut view of the display assembly.

As in detail illustrated in FIG. 17, a proximal end of the drive sleeve 30 is rigidly connected and fixed to a distal end portion of a dose setting sleeve 50, which in proximal direction 2 extends into or almost through a proximal threaded shaft portion 61 of a proximal base member 60. The dose setting sleeve 50 comprises at least one radially outwardly extending protrusion 57 to engage with a correspondingly shaped indentation or with a respective latch element 42 of the drive sleeve 30. In this way, the dose setting sleeve 50 and the drive sleeve 30 can be rigidly attached in axial direction to transfer a distally directed thrust from the dose setting sleeve 50 towards the drive sleeve 30.

Additionally and as shown in FIG. 6, dose setting sleeve 50 and drive sleeve 30 are also rotatably engaged by mutually corresponding connecting portions. Here, the drive sleeve 30 comprises a non-circular shaped receptacle 39a to receive a correspondingly shaped connector 53 of the dose setting sleeve 50. In this way also a rotation of the dose setting sleeve 50 unalterably transfers into a respective rotation of the drive sleeve 30.

Figure 14:
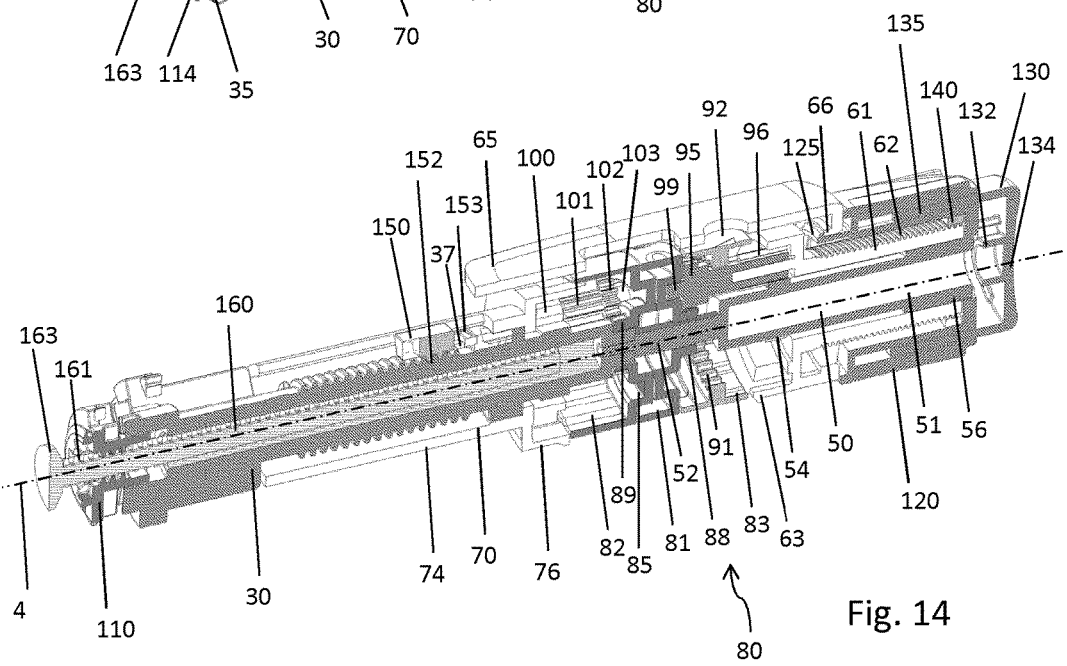
FIG. 14 shows the drive mechanism in a perspective illustration in a longitudinal cross section, FIG. 15 provides another longitudinal cross section through the drive mechanism.

The drive mechanism 3 further comprises a display assembly 80 which is illustrated in detail in FIGS. 14 and 17. The display assembly 80 comprises a first dose indicating member 81 and a second dose indicating member 82. The dose indicating members 81, 82 comprise a disc-like or sleeve-like shape and both comprise annular display surfaces 86, 87 to visually display variable dose sizes through a window 68 of a cover portion 65 or through a sidewall portion of the housing 20.

The first dose indicating member 81 comprises a first display surface 86 while the second dose indicating member 82 comprises a second annular display surface 87. While the first display surface 86 represents single units of the medicament to be dispensed and therefore comprises numerals from 0-9 the second dose indicating member 82, in particular its display surface 87 comprises numerals from 0, 1, 2, and so on thereby representing decades or tens, such like 10, 20 so on. If the drive mechanism 3 is for instance adapted to set and to inject a maximum dose of insulin of e.g. 120 IU, the numbers present on the second annular display surface 87 range from 1-12.

The two dose indicating members 81, 82 are both rotatably arranged on the longitudinal axis 4 and may be rotated in a dose incrementing direction 5 during dose setting and in an opposite direction, hence in dose decrementing direction 6 during dose dispensing. Accordingly, the numbers showing up in the window 68 either constantly increase or constantly decrease during dose setting and dose dispensing.

Moreover, the first dose indicating member 81 comprises a central orifice 81a and the second dose indicating member 82 comprises a second central orifice 82a. Said orifices 81a, 82a axially flush and are adapted to receive the dose setting sleeve 50 and/or the drive sleeve 30 as becomes apparent from the sketch of FIG. 17. Even though the assembly of dose setting sleeve 50 and drive sleeve 30 extends through both dose indicating members 81, 82, there is only an indirect transfer of angular momentum between dose setting sleeve 50, drive sleeve 30 and the two dose indicating members 81, 82.

In particular, the first and second dose indicating members 81, 82 are axially fixed relative to the housing 20 and/or relative to the proximal base member 60 and/or to the distal base member 70 as for instance illustrated in FIG. 17. In contrast to that, the assembly of drive sleeve 30 and dose setting sleeve 50 is axially displaceable relative to both dose indicating members 81, 82 for switching the drive mechanism 3 between the dose setting mode and the dose dispensing mode.

Figure 7:
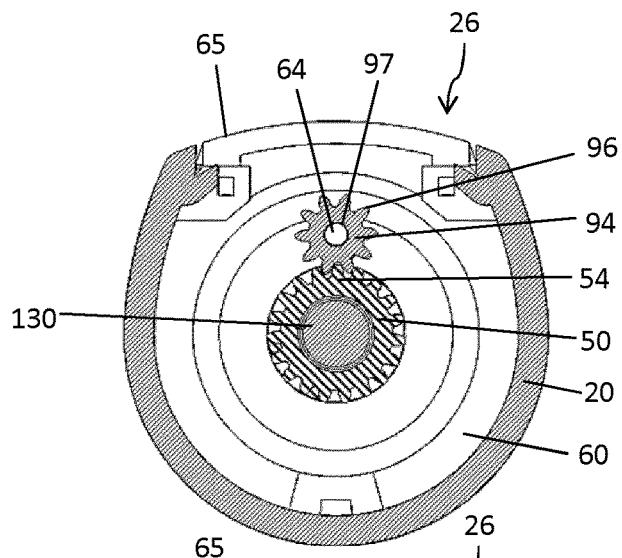
FIG. 7 shows a cross-section along E-E according to FIG. 1.
Figure 8:
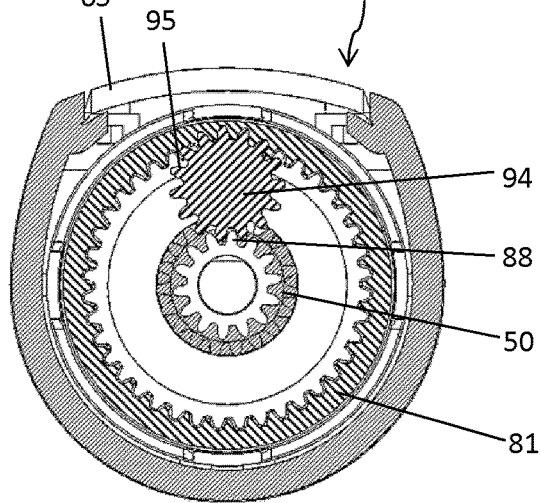
FIG. 8 shows a cross-section along F-F according to FIG. 1.

In order to transfer a driving torque between dose setting sleeve 50, drive sleeve 30 and at least one of first and second dose indicating members 81, 82 there are provided first and second display wheels 94, 100. As indicated in FIGS. 17 and 7 the dose setting sleeve 50 comprises a first geared portion 54 that meshes with a correspondingly shaped proximally located geared section 96 of the first display wheel 94. Said display wheel 94 further comprises a proximally located pocket hole or receptacle 97 to receive a distally and axially extending pin or bearing 64 of the proximal base member 60. Distally offset from the proximal geared section 96 the first display wheel 94 further comprises a distal geared section 95 that meshes with a central gear 88 of the first dose indicating member 81. In this way, a dose incrementing or dose decrementing rotation of the dose setting sleeve 50 can be transferred into a respective rotation of the first dose indicating member 81. The first dose indicating member 81 and the second dose indicating member 82 are only indirectly rotatably engaged via the drive sleeve 30 and the dose setting sleeve 50.

Figure 19:
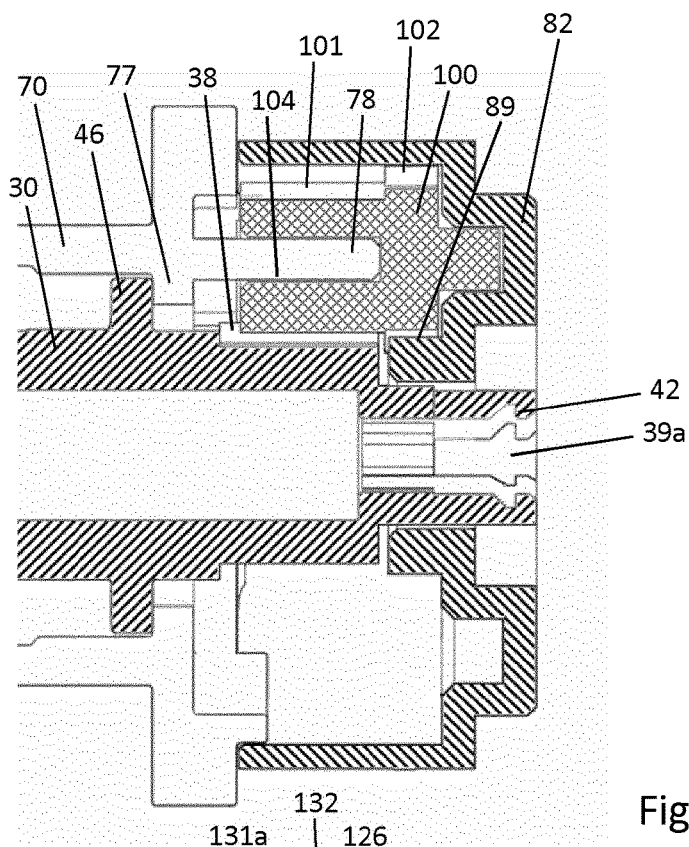
FIG. 19 shows a longitudinal and enlarged cross section through a proximal portion of the display assembly.

Hence, the second dose indicating member 82 is rotatably engaged with the drive sleeve 30 by means of the second display wheel 100. Similar as the first display wheel 94 also the second display wheel 100 is located radially offset from the longitudinal central axis 4 but is located radially inward compared to the display surface 86, 87 of first and/or second dose indicating members 81, 82. Also the second display wheel 100 is rotatably supported on an axially but proximally extending pin or bearing 78 of the distal base member 70 as indicated in FIG. 19. A distally located geared section 101 of the second display wheel 100 meshes with a radially outwardly extending tappet 38 of the drive sleeve 30 as indicated in FIG. 5. In this way, a continuous rotation of the drive sleeve 30 transfers to a discrete and stepwise rotation of the second display wheel 100.

The second display wheel 100 further comprises a proximally located geared section 102 that meshes with a central gear 89 of the second dose indicating member 82.

In the present embodiment according to FIG. 5 the drive sleeve 30 comprises two oppositely located tappets 38. Accordingly, during a complete revolution of the drive sleeve 30, the second dose indicating member 82 is subject to two consecutive discrete stepwise rotations.

By means of first and second display wheels 94, 100 extending parallel to the longitudinal axis 4 and hence parallel to the drive sleeve 30 and dose setting sleeve 50, the dose setting sleeve 50 and the drive sleeve 30 always rotate in the same sense of rotation as the first and second dose indicating members 81, 82.

Moreover and as illustrated in FIG. 17 the first dose indicating member 81 comprises a first annular groove 84 that is open towards the proximal direction 2 while the second dose indicating member 82 comprises a second annular groove 85 that is open towards the distal direction. Both annular grooves 84, 85 are particularly adapted to receive a pin 99, 103 of first and second display wheels 94, 100, respectively. In this way, the distal end of the first display wheel 94 can be radially constrained by the first dose indicating member 81 while a proximal end of the second display wheel 100 can be radially confined by the second dose indicating member 82.

Figure 18:
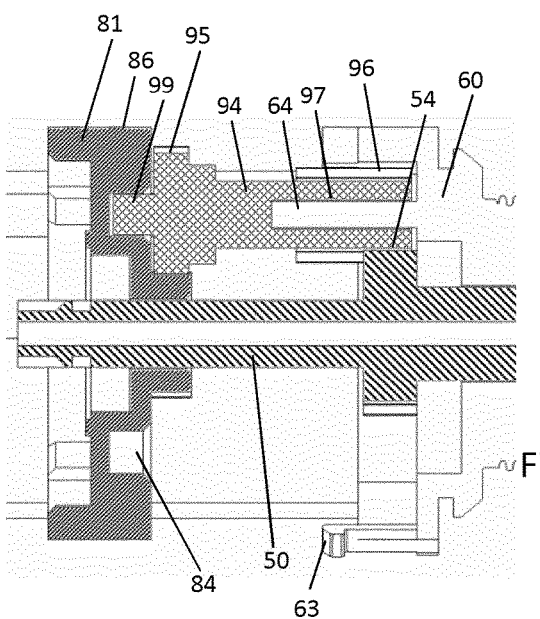
FIG. 18 shows a longitudinal and magnified cross section through a proximal portion of the display assembly.

Since the two dose indicating members 81, 82 directly abut in axial direction the first as well as the second dose indicating member 81, 82 can be axially constrained and axially supported by their respective first and second display wheels 94, 100. As indicated in FIG. 18, the first display wheel 94 with its pocket hole 97 axially abuts with the distally extending bearing 64 of the proximally located base member 60. The oppositely located pin 99 is in axial engagement with the annular groove 84 of the first dose indicating member 81. In a corresponding way also the pocket hole 104 of the second display wheel 100 receives the proximally extending bearing 78 of the distal base member 70 thereby supporting the second dose indicating member 82 by means of an axial abutment of its proximal pin 103 with the annular groove 85 of the second dose indicating member 82.

In this way, the first dose indicating member 81 can be axially supported in proximal direction 2 by the first display wheel 94 while the second dose indicating member 82 can be axially supported in distal direction 1 by means of the second display wheel 100. When interconnecting the two base members 60, 70 the first and second dose indicating members 81, 82 mutually abut and are therefore axially constrained and axially fixed relative to first and/or second base members 60, 70. In embodiments, wherein the first and second base members are fixedly attached to the housing 20, first and second dose indicating members 81, 82 are also axially constrained and fixed to the housing 20.

The first and the second display wheels 94, 100 remain permanently engaged with the dose setting sleeve 50 and the drive sleeve 30, respectively. Hence, the axial elongation of the respective geared sections 96, 101 of first and second display wheel 94, 100 allows for a distally directed displacement of drive sleeve 30 and dose setting sleeve 50 for switching the drive mechanism 3 between dose dispensing mode and dose setting mode.

Having a proximal base member 60 and a distal base member 70 allows for an almost complete assembly of the drive mechanism 3 before the drive mechanism 3 in its entirety is inserted into and fixed to the housing 20. As further illustrated in FIG. 15 the distal base member 70 comprises a radially widened receptacle portion 76 at its proximal end to receive and to support the display assembly 80.

Additionally, the display assembly 80 further comprises a third dose indicating member 83 that is axially offset from first and second dose indicating members 81, 82. In the present embodiment as illustrated in FIGS. 13 and 17 the third dose indicating member 83 also comprises an annular shape and features a third display surface 92 that is discernable through another window 67 of the cover portion 65 of the proximal base member 60. The third display surface 92 features a symbol or a color to visually indicate to the user whether the device 10 is in an idle state and is ready for setting of a dose or whether a dose setting or dose dispensing process is actually in progress.

Figure 9:
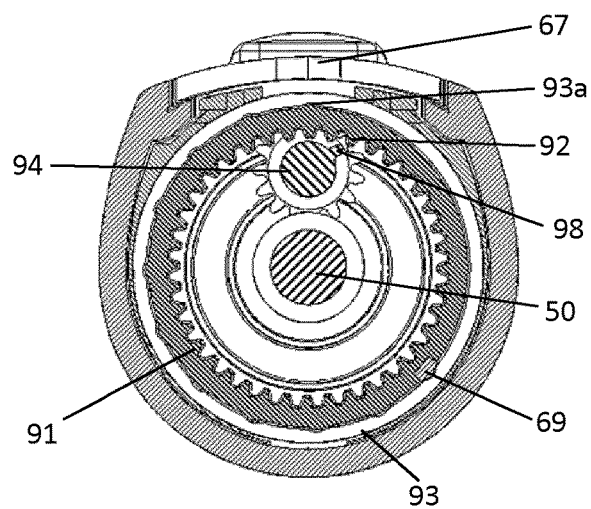
FIG. 9 shows a cross-section along G-G according to FIG. 1.

The third dose indicating member 83 comprises a geared rim 91 on its inside facing sidewall portion that is adapted to engage with a radially outwardly extending tappet 98 of the first display wheel 94 as indicated in FIG. 9. The tappet 98 is located axially between the distal geared section 95 and the proximal geared section 96 of the first display wheel.

The second as well as the third display wheel 82, 83 further comprise or interact with a retaining structure for keeping the respective dose indicating member 82, 83 in a particular rotational position when the tappet 98 of the first display wheel 94 and hence the tappet 38 of the drive sleeve 30 is actually disengaged from the retaining structure 93 or from the geared section 101 of the display wheel 100. As illustrated in FIGS. 1 and 9 the proximal base member 60 comprises a distally extending retaining member 69 of pin-like shape and featuring a radially outwardly extending bulged portion to engage with a correspondingly shaped recess 93a of the third dose indicating member's 83 retaining structure 93.

The circumferential distance of adjacent recesses 93a corresponds to the mutual engagement of the geared rim 91 and the tappet 98. In this way, discrete and stepwise rotation of the third dose indicating member 83 always starts and ends with a mutual engagement of the retaining member 69 with the retaining structure 93. In this way, the third dose indicating member 83 can be rotatably secured to the base member 60 and hence to the housing 20 if the tappet 98 even when the first display wheel 94 is disengaged from the geared rim 91 of the third dose indicating member 83.

In a similar way also the second dose indicating member 82 can be rotatably secured to the distal base member 70. As indicated in FIGS. 5 and 6, the base member 70 comprises a radially outwardly extending annular shaped retaining structure 72 featuring various radially outwardly but circumferentially spaced protrusions 73. As shown in FIGS. 5 and 6, the second dose indicating member 82 comprises a correspondingly shaped inside facing recessed structure with numerous recesses 87a that correspond and engage with the radially outwardly extending protrusion 73 of the base member 70. Also here, the mutually corresponding recesses 87a and protrusions 73 serve to provide a stepwise and consecutive securing or engagement of the second dose indicating member 82 with the base member 70.

From the sketches of FIGS. 5, 7 and 14 also the mutual assembly of the proximal base member 60 with the housing 20 becomes apparent. The housing 20 comprises a longitudinally extending slot or recess 26 at its proximal end to receive the cover portion 65 of the proximal base member 60. At circumferential side edges of the recess 26 the housing 20 comprises radially inwardly located prongs 25 extending from opposite sides at least partially into the recess 26 in tangential or circumferential direction. Here, the prongs 25 provide a radial support structure for the cover portion 65. Additionally, the prongs 25 extend radially inwardly from the inner sidewall of the housing 20 and may therefore engage with a correspondingly shaped recess 75 of an arc-shaped fixing portion 79 of the distal base member 70.

By means of this positive engagement the proximal as well as the distal base members 60, 70 can be rotatably fixed to the housing 20. Moreover, as illustrated in FIG. 14 the proximal base member 60 comprises at least one distally extending and radially deformable fastening element 63 by way of which the proximal base member 60 can be axially fixed to the housing 20. In particular, the proximal base member 60 can be clipped to the housing 20 while the distal base member 70 may axially abut against a radially stepped or recessed portion of the housing 20.

As shown in detail in FIGS. 14 and 15 the proximal base member 60 comprises a proximal shaft portion 61 featuring an outer thread 62. Additionally and radially offset from said shaft portion 62, the proximal base member 60 comprises a radially inwardly extending flange portion 66 adapted to engage with a fastening element 125 of a dose setting member 120. As indicated in FIG. 14, the sleeve-shaped dose setting member 120 comprises a latch-like radially resiliently deformable fastening element 125 to engage with the indentation formed by the radially inwardly extending flange portion 66 of the proximal base member 60. In this way, the dose setting member 120 can be axially fixed to the base member and may freely rotate relative to the base member.

Additionally, there is provided a cup-shaped dose dispensing member 130. Said dose dispensing member 130 may be permanently rotatably engaged with the sleeve like dose setting member 120 as becomes apparent from the cross-section according to FIG. 3. The dose dispensing member 130 acting as a dose button comprises an axially extending shaft portion 132 extending towards a proximal end of a proximal sleeve portion 51 of the dose setting sleeve 50 extending through the hollow proximal shaft portion 61 of the proximal base member 60.

Figure 3:
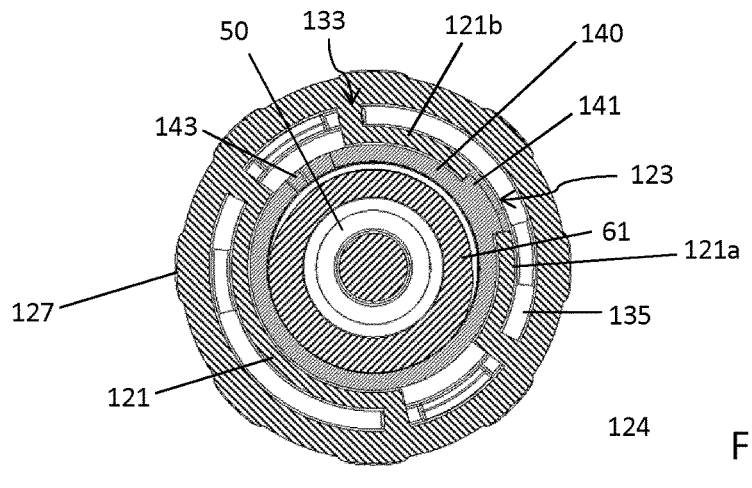
FIG. 3 shows a cross-section along A-A according to FIG. 1.

The dose setting member 120 comprises an annular cross-section featuring various grip structures 127 at its outer surface. The dose setting member 120 further comprises various radially inwardly extending protrusions 124 extending into circumferentially extending arched portions 121, 121a, 121b as illustrated in FIG. 3. Here, the protrusions 124 may act as bridging portions for integrally connecting the inner arched portion 121 with the outer sleeve portion of the dose setting member 120. Between arched portions 121a, 121b there is formed an axially extending slot or recess 123 to receive a radially outwardly extending protrusion 141 of a last dose limiting member 140.

As indicated in FIGS. 3 and 14 said last dose limiting member 140 is radially sandwiched between the proximal base member 60, in particular between its proximal shaft portion 61 and the dose setting member 120. The last dose limiting member 140 comprises an inner thread 142 threadedly engaged with the outer thread 62 of the proximal base member 60. In this way, the annular shaped last dose limiting member 140 is subject to a rotation relative to the base member 60 when the dose setting member 120 is dialled either in a dose incrementing direction 5 or dose decrementing direction 6s.

Due to the axially elongating recess 123 of the dose setting member 120 the last dose limiting member 140 is allowed to travel in axial direction as the dose setting member 120 is rotated.

Figure 20:
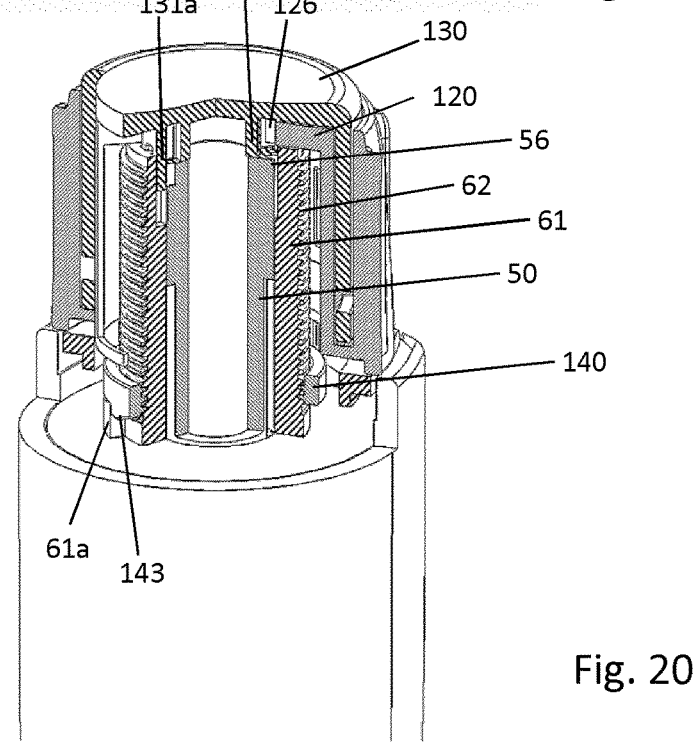
FIG. 20 shows a partially cut and perspective view of the proximal end of the drug delivery device with a depressed dose dispensing member.

The last dose limiting member 140 further comprises a radial stop 143 to engage with a correspondingly shaped radial stop 61a of the base member 60 when reaching an end-of-content configuration which is illustrated in FIG. 20.

As illustrated in detail in FIG. 15, the dose dispensing member 130 extends with a sidewall portion 135 between the inner arched portions 121, 121a, 121b of the dose setting member 120 and the outer sidewall portion 128 of the dose setting member 120. Moreover, and as illustrated in FIG. 15 the dose dispensing member 130 comprises at least one or several axially extending spring elements 136 to abut against a bottom portion 129 of the dose setting member 120. Said bottom portion 129 may radially extends between and may connect the arched portions 121 with the radially outwardly located sidewall portion 128 of the dose setting member 120.

In this way the dose dispensing member 130 can be axially displaced in distal direction 1 relative to the dose setting member 120 against the action of the at least one spring element 136. This spring element 136 is of particular use to bring and to transfer the dose dispensing member 130 into a proximal dose setting configuration as for instance illustrated in FIG. 15.

For transferring the drive mechanism 3 from the dose setting mode into the dose dispensing mode a user simply depresses the dose dispensing member 130 in distal direction 1. Then, the shaft portion 132 thereof axially abuts with a proximal end of the dose setting sleeve 50 thereby displacing the dose setting sleeve 50 in distal direction 1. Since the dose setting sleeve 50 is axially rigidly connected with the drive sleeve 30 also the drive sleeve 30 experiences a respective distally directed displacement until it reaches the distal dose dispensing configuration, in which the drive sleeve 30 is liberated from the housing 20 and in which the drive sleeve 30 is free to rotate under the action of the helical spring element 43.

Moreover, by displacing the dose dispensing member 130 in distal direction 1 a geared portion 131 of the axially extending shaft portion 132 of said dose dispensing member 130 is adapted to rotatably lock to the proximal base member 60, thereby inhibiting a potential rotation of the dose dispensing member 130 relative to the base member 60 or relative to the housing 20.

Since the dose dispensing member 130 is permanently rotatably locked to the dose setting member 120 by the radially inwardly extending protrusions 124 extending through respective recesses or slots 133 of the dose dispensing member 130 also the dose setting member 120 is rotatably locked to the base member 60 when the dose setting member 120 is in its distal dose dispensing position. Due to the rotational interlocking of the dose setting member 120 relative to the base member 60 the dose setting member 120 cannot rotate during a dose dispensing procedure. In this way also the last dose limiting member 140 cannot be rotated or axially displaced during a dose dispensing procedure.

Moreover, as indicated in FIG. 15 the dose setting member 120 comprises a radially inwardly extending flange portion 126 at its proximal end featuring a central through opening with a radially inwardly extending geared structure 126a. Said geared structure 126a is rotatably engaged with a correspondingly shaped geared portion 56 of the proximal sleeve portion 51 of the dose setting sleeve 50. When located in proximal dose setting position the dose setting sleeve 50 is hence rotatably locked or rotatably engaged with the dose setting member 120. A rotation of the dose setting member 120 relative to the base member 60 therefore leads to a respective rotation of the dose setting sleeve 50 and hence to a respective rotation of the drive sleeve 30.

By displacing the dose dispensing member 130 in distal direction 1 and by correspondingly displacing the dose setting sleeve 50 in its distal dose dispensing position the dose setting sleeve 50 is operably disengaged from the dose setting member 120. At the same time, or even prior to the disengagement of dose setting sleeve 50 and dose setting member 120 the dose dispensing member 130 rotatably locks to the proximal base member 60.

In this way the dose setting member 120 is only rotatable when the drive mechanism 3 is in dose setting mode. Due to the decoupling of the dose setting sleeve 50 from the dose setting member 120 during a dose dispensing the axial position of the last dose limiting member 140 reflects the sum of doses consecutively set and dispensed by the drive mechanism.

In the following setting of a dose if described.

For setting of a dose a user simply dials the dose setting member 120 in dose incrementing direction 5. Due to its rotational engagement with the dose setting sleeve 50 also said dose setting sleeve 50 together with the drive sleeve 30 are rotated accordingly against the action of the helical spring element 43. Said rotational displacement is secured by the drive sleeve's 30 ratchet member 32. Here, the ratchet member 32 provides an audible feedback to the user as it meshes along consecutive radially inwardly extending teeth 22 of the first toothed profile 21 of the housing 20. Since the ratchet member 32 is resiliently deformable it is operable to generate a click sound when rotated relative to the teeth 22 of the first toothed profile 21. Additionally, at least the first dose indicating member 81 as well as the third dose indicating member 83 are rotated in a dose incrementing way, thereby illustrating to the user the size of the dose actually set.

Figure 10:
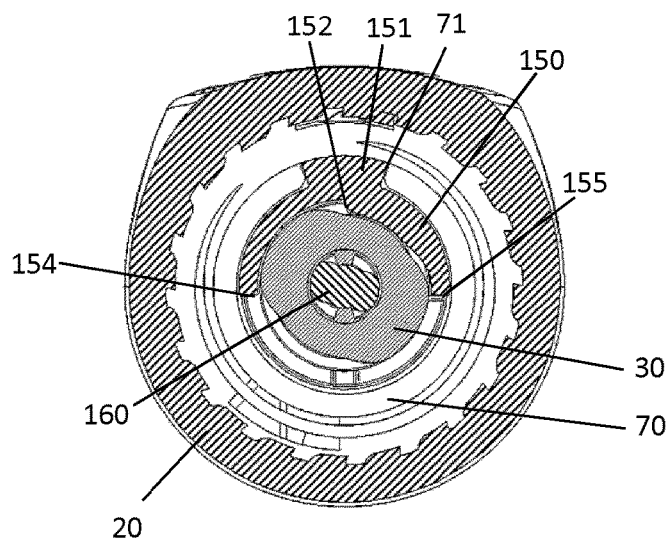
FIG. 10 shows a cross-section through the device along H-H according to FIG. 1

Moreover, and as becomes apparent from FIGS. 10 and 15, there is a provided a single dose limiting member 150 disposed radially between the drive sleeve 30 and the distal base member 70. Here, the arc-shaped or semicircular-shaped single dose limiting member 150 comprises a radially outwardly extending protrusion 151 engaged with a correspondingly radially outwardly extending and axially elongated recess 71 of a distal sleeve portion 74 of the base member 70. In this way, the single dose limiting member 150 is rotatably locked to the stationary base member 70 and may only slide along the axially extending groove or recess 71 thereof during a dose incrementing or a dose decrementing rotation 5, 6 of the drive sleeve 30.

Additionally and as illustrated in FIG. 15 the drive sleeve comprises an outer threaded portion 31 engaged with an inner thread 152 of the single dose limiting member 150. It is due to the keyed or splined engagement of the single dose limiting member 150 with the distal base member 70 and due to the threaded engagement of the single dose limiting member 150 with the drive sleeve 30 that a rotation of the drive sleeve 30 transfers to an axial displacement of the single dose limiting member 150. The single dose limiting member 150 comprises at least one radial stop 154, 155, e.g. at its circumferential end to engage with a correspondingly shaped radial stop 36 of the drive sleeve 30, e.g. located near a distal end of its threaded portion 31. As the drive sleeve 30 is dialled and rotated in dose incrementing direction 5 the single dose limiting member 150 may advance in distal direction 1 until it engages with the distal stop 36 of the drive sleeve 30.

When mutually corresponding radial stop faces 155 and radial stop 36 get in direct abutment a further rotation of the drive sleeve 30 is effectively blocked due to the splined or keyed engagement of the single dose limiting member 150 with the distal base member 70. The axial position of the stop 36 as well as the lead of the threaded engagement of the single dose limiting member 150 and the drive sleeve 30 is adapted such that such a blocking configuration correlates to a maximum allowable dose size, of e.g. 120 IU of insulin.

The oppositely located radial stop 154 of the single dose limiting member 150 may act as a zero dose stop adapted to engage with another radial but proximally located stop 37 of the drive sleeve 30. Mutual engagement of the radial stop 154 of the single dose limiting member 150 with the proximally located stop 37 of the drive sleeve 30 effectively inhibits that a user may set a negative dose.

Additionally, the single dose limiting member 150 further comprises a resiliently deformable clicking member 153 that may at least occasionally audibly engage with the stop 37 of the drive sleeve 30 as the single dose limiting member 150 approaches a zero dose configuration, in particular when a dose dispensing procedure terminates. In this way, an audible feedback can be provided to a user that the drive mechanism 3 returns into an initial state. The clicking member is typically axially deformable and may therefore audibly engage the stop 37 drive sleeve 30 radially outwardly extending therefrom.

Since the single dose limiting member 150 is permanently threadedly engaged with the drive sleeve 30 it moves forth and back as the drive sleeve 30 is rotated in dose incrementing direction 5 during dose setting and as the drive sleeve 30 is rotated in the opposite, dose decrementing direction 6 during dose dispensing or dose correction.

After a dose of intended size has been set the drive mechanism 3 and hence the drug delivery device 10 is ready for dispensing of said dose.

In the following dispensing of a dose is described

The dispensing procedure is started by depressing the dose dispensing member 130 in distal direction 1. Then, the dose dispensing member 130 rotatably locks to the proximal base member 60 and therefore also locks a rotation of the dose setting member 120 relative to the proximal base member 60. As shown in FIG. 20 the dose dispensing member 130 comprises a distally extending pin 131a to engage with a correspondingly shaped recessed structure (not illustrated) of the proximal base member 60. When depressing the dose dispensing member 130 in distal direction it rotatably locks to the proximal base member 60 by means of the pin 131a, thereby also impeding a further rotation of dose setting member 120 when the device 10 is in dose dispensing mode. By means of this kind of interlocking misuse of the device, hence dialling of the dose setting member during dose dispensing is effectively prevented.

The axial position of the last dose limiting member 140 is then fixed at least during the duration of the dose dispensing procedure. Additionally, the distally extending shaft portion 132 axially abuts with the dose setting sleeve 50 and drives the dose setting sleeve 50 out of engagement from the dose setting member 120. Since the axial displacement of the dose setting sleeve 50 is directly and unalterably transferred to the drive sleeve 30 the drive sleeve 30 will engage with its crown wheel 40 with the correspondingly shaped crown wheel 114 of the drive wheel 110.

After or as soon as a torque transmitting coupling of drive sleeve 30 and drive wheel 110 is established the ratchet member 32, e.g. integrally formed with the drive sleeve 30, also disengages from the first toothed profile 21 of the housing 20, thereby liberating and releasing the rotation of the drive sleeve 30. Consequently, the drive sleeve 30 and hence the drive wheel 110 start to rotate in the dose decrementing direction 6 under the effect of the helical spring element 43 previously strained and biased during dose setting.

As already described, not only the piston rod 160 is driven in distal direction 1 by the revolutions of the drive wheel 110 but also the single dose limiting member 150 returns into its initial position until its radial stop 154 engages with a corresponding radial stop 37 of the drive sleeve. Additionally, the clicking element 153 audibly engages with the stop 37 of the drive sleeve in order to audibly indicate to a user that a dose dispensing procedure just terminated.

During the entire dose injection or dose dispensing process it is required that the user keeps the dose dispensing member 130 depressed against the action of the retention spring element 35 of the drive sleeve 30. When releasing the dose dispensing member 130 the drive sleeve 30 as well as the dose setting sleeve 50 interconnected therewith return into their proximal dose setting position which is e.g. characterized by a radially outwardly extending flange portion 46 of the drive sleeve 30 that axially abuts with a correspondingly shaped radially inwardly extending flange portion 77 of the distal base member 70 as illustrated for instance in FIG. 15. This proximally directed displacement of the drive sleeve 30 and the dose setting sleeve 50 also disengages the rotational interlock of the dose dispensing member 130 and the proximal base member 60. As a consequence, the dose setting member 120 may be repeatedly rotated for setting of a consecutive dose.

As it becomes further apparent from FIG. 11 a dose decrementing rotation of the drive wheel 110 during a dose dispensing procedure is typically accompanied by the interlocking member 111 meshing with the ratchet teeth 24 of the second toothed profile 23. Dose decrementing rotation of the drive wheel 110 is therefore accompanied with an audible feedback, e.g. in form of a clicking noise indicating to a user of the device 10 that a dose dispensing procedure is actually in progress.

Figure 21:
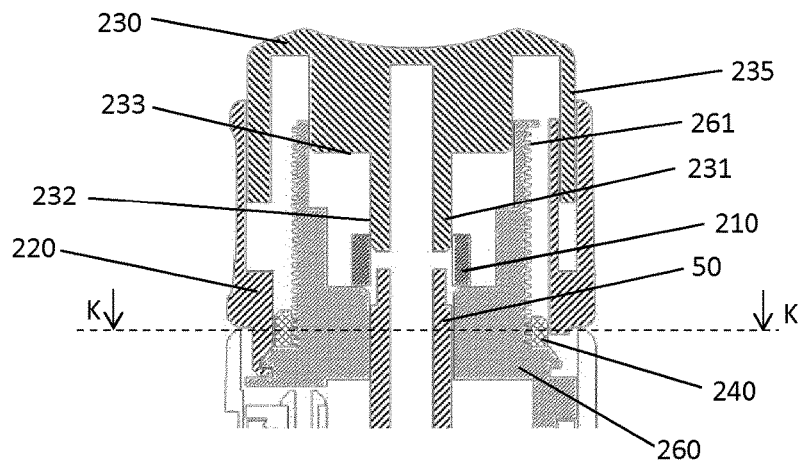
FIG. 21 shows an enlarged view of a proximal end of the drive mechanism according to an alternative embodiment and FIG. 22 shows a cross-section K-K through the embodiment according to FIG. 21.
Figure 22:
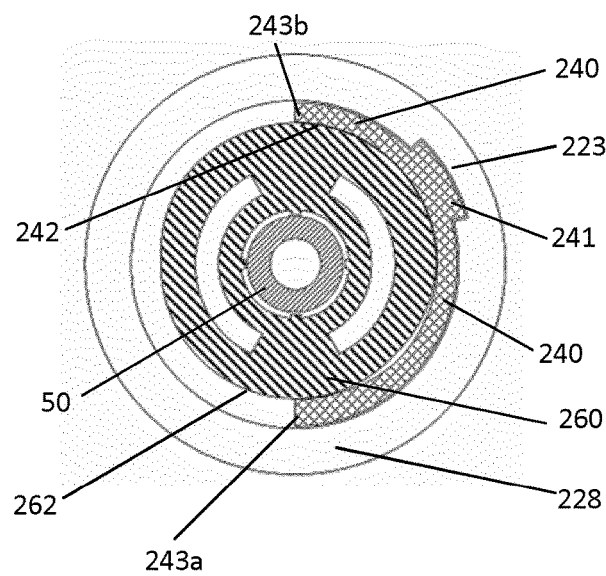

In FIGS. 21 and 22 an alternative embodiment is illustrated, wherein the last dose limiting member 240 only comprises a semi-circular, arched shape with oppositely located radial stop portions 243a, 243b to engage with correspondingly shaped radial stop portions of the proximal base member 260. Also here, the proximal base member 260 comprises a proximally extending shaft portion 261 featuring an outer thread 262 to engage with an inner thread 242 of the last dose limiting member 240. The dose setting member 220 comprises a recess 223 at its inside facing sidewall portion 228 to receive the radially outwardly extending protrusion 241 of the last dose limiting member 240.

Also here, the dose dispensing member 230 comprises a distally extending shaft portion 231 to apply distally directed thrust to the co-aligned dose setting sleeve 50. The sidewall portions 235 and 228 of the dose dispensing member 230 and the dose setting member 220 are rotatably engaged, e.g. by mutually corresponding radially extending protrusions and recesses, that are not particularly illustrated here. In this way also a permanent rotational interlock of dose setting member 220 and dose dispensing member 230 can be attained.

For rotatably securing or rotatably interlocking the dose dispensing member 230 to the base member 260 the dose dispensing member 230 comprises a stepped portion 233 that may either comprise a crown wheel or radially outwardly extending gears to rotatably lock to the proximal base member 260 when distally displaced in dose dispensing position.

Additionally, there is provided a sleeve-shape transfer element 210 that serves as a torque transmitting coupling member between the dose setting sleeve 50 and the shaft portion 232 of the dose dispensing member 230. In the embodiment according to FIGS. 20 and 21 a user induced rotation of the outer dose setting member 220 is first transferred to a respective rotation to the dose dispensing member 230 and is then transferred via the dose dispensing member 230 and its distally extending shaft portion 232 via the transfer element 210 to the dose setting sleeve 50. By distally displacing the dose dispensing member 230 for dose dispensing the dose setting sleeve 50 is advanced and pushed in distal direction so as to disengage from the geared transfer element 210.

| List of Reference Numerals | |
| --- | --- |
| 1 | distal direction |
| 2 | proximal direction |
| 3 | drive mechanism |
| 4 | longitudinal axis |
| 5 | dose incrementing direction |
| 6 | dose decrementing direction |
| 10 | drug delivery device |
| 12 | cartridge |

-continued

List of Reference Numerals

| | |
|---|---|
| 13 | cartridge holder |
| 14 | piston |
| 16 | needle assembly |
| 17 | injection needle |
| 18 | needle cap |
| 19 | protective cap |
| 20 | housing |
| 21 | toothed profile |
| 22 | ratchet tooth |
| 23 | toothed profile |
| 24 | ratchet tooth |
| 25 | prong |
| 25a | flange portion |
| 26 | recess |
| 27 | guiding portion |
| 28 | orifice |
| 28a | protrusion |
| 29 | fixing member |
| 30 | drive sleeve |
| 31 | threaded portion |
| 32 | ratchet member |
| 33 | catch portion |
| 34 | bore |
| 35 | spring element |
| 36 | stop |
| 37 | stop |
| 38 | tappet |
| 39a | receptacle |
| 40 | crown wheel |
| 41 | crown tooth |
| 42 | latch element |
| 43 | spring element |
| 44 | distal end |
| 45 | proximal end |
| 46 | flange portion |
| 50 | dose setting sleeve |
| 51 | sleeve portion |
| 52 | shaft portion |
| 53 | connector |
| 54 | geared portion |
| 56 | geared portion |
| 57 | protrusion |
| 60 | base member |
| 61 | shaft portion |
| 61a | radial stop |
| 62 | outer thread |
| 63 | fastening element |
| 64 | bearing |
| 65 | cover portion |
| 66 | flange portion |
| 67 | window |
| 68 | window |
| 69 | retaining member |
| 70 | base member |
| 71 | recess |
| 72 | retaining structure |
| 73 | protrusion |
| 74 | sleeve portion |
| 75 | recess |
| 76 | receptacle |
| 77 | flange portion |
| 78 | bearing |
| 79 | fixing portion |
| 80 | display assembly |
| 81 | dose indicating member |
| 81a | central orifice |
| 82 | dose indicating member |
| 82a | central orifice |
| 83 | dose indicating member |
| 84 | annular groove |
| 85 | annular groove |
| 86 | display surface |
| 87 | display surface |
| 87a | recess |
| 88 | central gear |
| 89 | central gear |
| 91 | geared rim |

-continued

List of Reference Numerals

| | |
|---|---|
| 92 | display surface |
| 93 | retaining structure |
| 93a | recess |
| 94 | display wheel |
| 95 | geared section |
| 96 | geared section |
| 97 | pocket hole |
| 98 | tappet |
| 99 | pin |
| 100 | display wheel |
| 101 | geared section |
| 102 | geared section |
| 103 | pin |
| 104 | pocket hole |
| 110 | drive wheel |
| 111 | interlocking member |
| 112 | ratchet tooth |
| 113 | orifice |
| 114 | crown wheel |
| 115 | inner thread |
| 116 | latching element |
| 117 | protrusion |
| 118 | flange |
| 119 | crown tooth |
| 120 | dose setting member |
| 121 | arched portion |
| 121a | arched portion |
| 121b | arched portion |
| 123 | recess |
| 124 | protrusion |
| 125 | fastening element |
| 126 | flange portion |
| 126a | geared structure |
| 127 | gripping structure |
| 128 | sidewall |
| 129 | bottom portion |
| 130 | dose dispensing member |
| 131 | geared portion |
| 131a | pin |
| 132 | shaft portion |
| 133 | slot |
| 134 | proximal end phase |
| 135 | sidewall |
| 136 | spring element |
| 140 | last dose limiting member |
| 141 | protrusion |
| 142 | inner thread |
| 143 | radial stop |
| 150 | single dose limiting member |
| 151 | protrusion |
| 152 | thread |
| 153 | clicking element |
| 154 | radial stop |
| 155 | radial stop |
| 160 | piston rod |
| 161 | threaded portion |
| 162 | groove |
| 163 | pressure foot |
| 210 | transfer element |
| 220 | dose setting member |
| 223 | slot |
| 228 | sidewall portion |
| 230 | dose dispensing member |
| 231 | geared portion |
| 232 | shaft portion |
| 233 | stepped portion |
| 235 | sidewall portion |
| 240 | last dose limiting member |
| 241 | protrusion |
| 242 | inner thread |
| 243a | radial stop |
| 243b | radial stop |
| 260 | base member |
| 261 | shaft portion |
| 262 | outer thread |

The invention claimed is:

1. A drive mechanism of a drug delivery device for dispensing of a dose of a medicament, the mechanism comprising:
 an elongated housing extending in an axial direction;
 a piston rod to operably engage with a piston of a cartridge to displace the piston in axial distal direction;
 a drive wheel axially fixed to the housing, engaged with the piston rod and rotatable relative to the housing for driving the piston rod in distal direction; and
 a drive sleeve axially displaceable relative to the drive wheel to rotatably engage with the drive wheel in a distal dose dispensing position and to disengage from the drive wheel in a proximal dose setting position,
 wherein the drive sleeve is rotatably secured to the housing in the proximal dose setting position by a ratchet member.

2. The drive mechanism according to claim 1, wherein the drive sleeve is rotatable in a dose incrementing direction against the action of a spring element when in proximal dose setting position.

3. The drive mechanism according to claim 1, wherein the drive sleeve is rotatable in a dose decrementing direction against the action of the ratchet member when in proximal dose setting position.

4. The drive mechanism according to claim 1, wherein the ratchet member is radially resiliently deformable, and wherein the drive sleeve comprises the radially resiliently deformable ratchet member meshing with a first toothed profile of the housing when in the proximal dose setting position.

5. The drive mechanism according to claim 1, wherein the drive sleeve is displaceable in distal direction against the action of a retention spring element axially supported by the housing.

6. The drive mechanism according to claim 1, further comprising a dose dispensing member located at a proximal end of the housing, operably engaged with the drive sleeve and distally depressible relative to the housing to displace the drive sleeve into the distal dose dispensing position.

7. The drive mechanism according to claim 1, wherein the drive sleeve comprises a crown wheel at its distal end to engage with a corresponding crown wheel of the drive wheel.

8. The drive mechanism according to claim 1, wherein the drive wheel is rotatably locked to the housing with regard to a dose incrementing direction by an interlocking member engaged with a second toothed profile of the housing.

9. The drive mechanism according to claim 8, wherein the drive wheel is rotatable in a dose decrementing direction while the interlocking member audibly meshes with the second toothed profile.

10. The drive mechanism according to claim 1, wherein the drive wheel comprises a threaded orifice threadedly engaged with an outer threaded portion of the piston rod.

11. The drive mechanism according to claim 1, wherein the piston rod comprises an axially extending radial groove engaged with a radial protrusion of a housing's guiding portion.

12. The drive mechanism according to claim 1, wherein the drive sleeve is rotatable in a dose decrementing direction under the action of a spring element when the distal dose dispensing position to transfer a driving torque to the drive wheel.

13. The drive mechanism according to claim 1, further comprising a dose setting member rotatably supported on the housing at least in a dose incrementing direction to transfer a dose incrementing torque to the drive sleeve when in the proximal dose setting position.

14. The drive mechanism according to claim 13, wherein the dose setting member is rotatably locked to the housing and is rotatably decoupled from the drive sleeve when the drive sleeve is in dose dispensing position.

15. A drug delivery device for dispensing of a dose of a medicament, the device comprising:
 a drive mechanism comprising:
  an elongated housing extending in an axial direction;
  a piston rod to operably engage with a piston of a cartridge to displace the piston in axial distal direction;
  a drive wheel axially fixed to the housing, engaged with the piston rod and rotatable relative to the housing for driving the piston rod in distal direction; and
  a drive sleeve axially displaceable relative to the drive wheel to rotatably engage with the drive wheel in a distal dose dispensing position and to disengage from the drive wheel in a proximal dose setting position,
  wherein the drive sleeve is rotatably secured to the housing in the proximal dose setting position by a ratchet member; and
 a cartridge at least partially filled with the medicament and being arranged in the housing of the drive mechanism or in a cartridge holder fixed to the housing.

16. The drive mechanism according to claim 15, wherein the ratchet member is radially resiliently deformable, and wherein the drive sleeve comprises the radially resiliently deformable ratchet member meshing with a first toothed profile of the housing when in the proximal dose setting position.

17. The device according to claim 15, wherein the drive sleeve is displaceable in the distal direction against the action of a retention spring element axially supported by the housing.

* * * * *

UNITED STATES PATENT AND TRADEMARK OFFICE
CERTIFICATE OF CORRECTION

PATENT NO. : 10,105,493 B2
APPLICATION NO. : 14/783535
DATED : October 23, 2018
INVENTOR(S) : Stefan Bayer et al.

Page 1 of 1

It is certified that error appears in the above-identified patent and that said Letters Patent is hereby corrected as shown below:

In the Claims

In Column 30, Line 10 (approx.), in Claim 12, delete "when the" and insert -- when in the --

Signed and Sealed this
Twelfth Day of February, 2019

Andrei Iancu
*Director of the United States Patent and Trademark Office*